(12) United States Patent
Zipkin et al.

(10) Patent No.: US 8,372,888 B2
(45) Date of Patent: Feb. 12, 2013

(54) SPHINGOSINE KINASE TYPE 1 INHIBITORS, COMPOSITIONS AND PROCESSES FOR USING SAME

(75) Inventors: Robert E. Zipkin, Wynnewood, PA (US); Sarah Spiegel, Richmond, VA (US); Jeffrey Kroll Adams, Fort Washington, PA (US)

(73) Assignee: Enzo Therapeutics, Inc., Farmingdale, NY (US)

( * ) Notice: Subject to any disclaimer, the term of this patent is extended or adjusted under 35 U.S.C. 154(b) by 0 days.

(21) Appl. No.: 12/387,228

(22) Filed: Apr. 29, 2009

(65) Prior Publication Data
US 2010/0035959 A1 Feb. 11, 2010

Related U.S. Application Data

(60) Provisional application No. 61/048,638, filed on Apr. 29, 2008.

(51) Int. Cl.
*A61K 31/133* (2006.01)
(52) U.S. Cl. ........ 514/653; 514/649; 514/646; 514/579; 564/355; 564/336; 564/305
(58) Field of Classification Search ........................ None
See application file for complete search history.

(56) References Cited

U.S. PATENT DOCUMENTS

| | | | | |
|---|---|---|---|---|
| 3,871,958 | A * | 3/1975 | Nakazawa et al. | 435/106 |
| 4,707,440 | A | 11/1987 | Stavrianopoulos et al. | |
| 6,372,800 | B1 | 4/2002 | Fujita et al. | |
| 2004/0203104 | A1 * | 10/2004 | Spiegel et al. | 435/69.1 |
| 2007/0196493 | A1 * | 8/2007 | Klinski et al. | 424/486 |
| 2008/0145883 | A1 | 6/2008 | Baumruker et al. | |
| 2008/0167352 | A1 | 7/2008 | Smith et al. | |
| 2010/0233121 | A1 * | 9/2010 | Frohna | 424/85.4 |

OTHER PUBLICATIONS

"Practical and highly stereoselective approaches to the total synthesis of (−)-codonopsinine" by Chandrasekhar et al., Tetrahedron: Asymmetry 17, 1380-86 (2006).*
"Efficient stereodivergent synthesis of erythro- and threo-sphingosines: unprecedented reversal of the stereochemistry in the addition" by Murakami et al., Tetrahedron 58, 9257-63 (2002).*
"Syntheses of sphingosine-1-phosphate analogues and their interaction with EDG/S1P receptors" by Lim et al., Bioorg. Med. Chem. Lett. 14, 2499-503 (2004).*
"Synthesis and biological properties of novel sphingosine derivatives" by Murakami et al., Bioorg. Med. Chem. Lett. 15, 1115-19 (2005).*
"Synthesis and Cytotoxicity of New Aromatic Ceramide Analogs with Alkylsulfonamido Chains" by Kim et al., Arch. Pharm. Res. 30, 570-80 (2007).*
"Synthesis and Biological Evaluation of Ceramide Analogues with Substituted Aromatic Rings or an Allylic Fluoride in the Sphingoid Moiety" by Overmeire et al., J. Med. Chem. 43, 4189-99 (2000).*
"Structure-Activity Relationship of Short-Chain Sphingoid Bases as Inhibitors of Sphingosine Kinase" by de Jonghe et al., Bioorg Med. Chem. Lett. 9, 3175-80 (1999).*
"Hard Gelatin Capsule Formulation Development" by Guo et al., Pharm. Tech. 44-60 (2002).*
"Pharmaceutical Salts" by Berge et al., J. Pharm. Sci. 66, 1-19 (1977).*
Amarente-Mendes et al., Bcr-Abl exerts its antiapoptotic effect against diverse apoptotic stimuli through blockage of mitochondrial release of cytochrome C and activation of caspase-3, Blood 1998, 1700-1705, 91.
Baran et al., Alterations of ceramide/sphingosine 1-phosphate rheostat involved in the regulation of resistance to imatinib-induced apoptosis in k562 human chronic myeloid luekemia cells, JBC 2007, 10922-10934, 282.
Berdyshev et al., De novo biosynthesis of dihydrosphingosine-1-phosphate by sphingosine kinase 1 in mammalian cells, Cell Signal 2006, 1779-1792, 18.
Betito et al., Regulation by sphingosine-1-phosphate of Bax and Bad activities during apoptosis in a MEK-dependent manner, Biochem Biophys Res Commun 2006, 1273-1277, 340.
Bonhoure et al., Overcoming MDR-associated chemoresistance in HL-60 acute myeloid leukemia cells by targeting sphingosine kinase-1, Leukemia 2006, 95-102, 20.
Brinkman, Volker, Sphingosine 1-phosphate receptors in health and disease: mechanistic insights from gene deletion studies and reverse pharmacology, Pharmacol Ther 2007, 85-105, 115.
Cheng et al., Conversion of Bcl-2 to a Bax-like death effector by caspases, Science 1997, 1966-1968, 278.
Cuvillier et al., Suppression of ceramide-mediated programmed cell death by sphingosine-1-phosphate, Nature 1996, 800-803, 381.
Cuvillier et al., Sphingosine 1-phosphate inhibits activation of caspases that cleave poly(ADP-ribose) polymerase and lamins during Fas- and ceramide-mediated apoptosis in Jurkat T lymphocytes, JBC 1998, 2910-2916, 273.
Cuvillier et al., Sphingosine 1-phosphate antagonizes apoptosis of human leukemia cells by inhibiting release of cytochrome C and Smac/DIABLO from mitochondria, Blood 2001, 2828-2836, 98.
Cuvillier et al., Involvement of sphingosine in mitochondria-dependent Fas-induced apoptosis of Type II Jurkat T cells, JBC 2000, 15691-15700, 275.
Dai et al., Pharmacological inhibitors of the mitogen-activated protein kinase (MAPK) kinase/MAPK cascade interact synergistically with UCN-01 to induce mitochondrial dysfunction and apoptosis in human leukemia cells, Cancer Res 2001,5106-5115, 61.
De Jonghe et al., Structure-activity relationship of short chain sphingoid bases as inhibitors of sphingosine kinase, Bioorg Med Chem Lett 1999, 3175-3180, 9.
De Luca et al., NAD+/NADH as/or CoQ/CoQH2 ratios from plasma membrane electron transport may determine ceramide and sphingosine-1-phosphate levels accompanying G1 arrest and apoptosis, Biofactors 2005, 43-60, 25.

(Continued)

*Primary Examiner* — Anish Gupta
*Assistant Examiner* — Theodore R West
(74) *Attorney, Agent, or Firm* — Elie Gendloff, Esq.

(57) ABSTRACT

Provided are novel compositions which uniquely inhibit sphingosine kinase Type 1 (SphK1) and which are useful in a number of applications including killing or damaging cancer cells, inducing apoptosis, inhibiting growth, metastasis and development of chemoresistance in cancer cells, leukemia, increasing the effectiveness of anti-cancer agents, attenuating immune reactivity, inhibiting survival signaling in cancer cells, and reducing symptoms of multiple sclerosis.

5 Claims, 18 Drawing Sheets

OTHER PUBLICATIONS

Edsall et al., N,N-dimethylsphingosine is a potent competitive inhibitor of sphingosine kinase but not of protein kinase C: modulation of cellular levels of sphingosine 1-phosphate and ceramide, Biochemistry 1998, 12892-12898, 37.
Filipits et al., Drug resistance factors in acute myeloid leukemia: a comparative analysis, Leukemia 2000, 68-76, 14.
French et al., Discovery and evaluation of inhibitors of human sphingosine kinase, Cancer Res 2003, 5962-5969, 63.
Gamble et al., Phenoxodiol, an experimental anticancer drug, shows potent antiangiogenic properties in addition to its antitumour effects, Int. J. Cancer 2006, 2412-2420, 118.
Hait et al., Sphingosine kinases, sphingosine 1-phosphate, apoptosis and diseases, Biochim Biophys Acta 2006, 2016-2026, 1758.
Hait et al., Role of sphingosine kinase 2 in cell migration toward epidermal growth factor, JBC 2005, 29462-29469, 280.
Hamada et al., Involvement of Mac-1-mediated adherence and sphingosine 1-phosphate in survival of phorbol ester-treated U937 cells, Biochem Biophys Res Commun 1998, 745-750, 244.
Igarashi et al., Effect of chemically well-defined sphingosine and its N-methyl derivatives on protein kinase C and src kinase activities, Biochemistry 1989, 6796-6800, 28.
Jarvis et al., Induction of apoptotic DNA damage and cell damage and cell death by activation of the sphingomyelin pathway, PNAS USA 1994, 73-77, 91.
Jarvis et al., Evidence for involvement of mitogen-activated protein kinase, rather than stress-activated protein kinase, in potentiation of 1-beta-D-arabinofuranosylcytosine-induced apoptosis by interruption of protein kinase c signaling, Mol Pharmacol 1998, 844-856, 54.
Jarvis et al., Coordinate regulation of stress- and mitogen-activated protein kinases in the apoptotic actions of ceramide and sphingosine, Mol Pharmacol 1997, 935-947, 52.
Jendiroba et al., Effective cytotoxicity against human leukemias and chemotherapy-resistant leukemia cell lines by N-N-dimethylsphingosine, Leuk Res. 2002, 301-310, 26.
Johnson et al., Intrinsic cytotoxicity and chemomodulatory actions of novel phenethylisothiocyanate sphingoid base derivatives in HL-60 human promyelocytic leukemia cells, J. Pharmacol. Exp. Therap. 2004, 452-461, 309.
Kim et al., Synthesis and evaluation of sphingoid analogs as inhibitors of sphingosine kinases, Bioorg & Med Chem 2005, 3475-3485, 13.
Kohama et al., Molecular cloning and functional characterization of murine sphingosine kinase, JBC 1998, 23722-23728, 273.
Kohno et al., Intracellular role for sphingosine kinase 1 in intestinal adenoma cell proliferation, Mol Cell Biol 2006, 7211-7223, 26.
Kono et al., F-12509A, a new sphingosine kinase inhibitor, produced by a discomycete, J. Antibiotics 2000, 459-466, 53.
Kono et al., B-5354 a, b, and c, new sphingosine kinase inhibitors, produced by a marine bacterium; taxonomy, fermentation, isolation, physico-chemical properties and structure determination, J. Antibiotics 2000, 753-758, 53.
Li et al., Sphingosine kinase-1 mediates BCR/ABL-induced upregulation of mcl-1 in chronic myeloid leukemia cells, Oncogene 2007, 7904-7908, 26.
Liu et al., Molecular cloning and functional characterization of a novel mammalian sphingosine kinase type 2 isoform, JBC 2000, 19513-19520, 275.
Maceyka et al., Sphk1 and Sphk2, sphingosine kinase isoenzymes with opposing functions in sphingolipid mechanism, JBC 2005, 37118-37129, 280.
Maggio et al., The histone deacetylase inhibitor MS-275 interacts synergistically with fludarabine to induce apoptosis in human leukemia cells, Cancer Res. 2004, 2590-2600, 64.
Marsolais & Rosen, Chemical modulators of sphingosine-1-phosphate receptors as barrier-oriented therapeutic molecules, Nature Reviews/Drug Discovery 2009, 297-307, 8.
McCormack et al, Animal models of acute myelogenous leukaemia-development, application and future perspectives, Leukemia 2005, 687-706, 19.
Milstien & Spiegel, Targeting sphingosine-1-phosphate: a novel avenue for cancer therapeutics, Cancer Cell 2006, 148-150, 9.

Mitra et al., Role of ABCC1 in export of sphingosine-1-phosphate from mast cells, PNAS USA 2006, 16394-16399, 103.
Moulding et al., Apoptosis is rapidly triggered by antisense depletion of mcl-1 in differentiating U937 cells, Blood 2000, 1756-1763, 96.
Neviani et al., FTY720, a new alternative for treating blast crisis chronic myelogenous leukemia and Philadelphia chromosome-positive acute lymphocytic leukemia, J Clin Invest 2007, 2408-2421, 117.
Ng et al., Marked suppression of tumor growth by FTY720 in a rat liver tumor model: the significance of down-regulation of cell survival Akt pathway, Int J Oncol 2007, 375-380, 30.
Niiro et al., (3z)-2-acetylamino-3-octadecen-1-ol as a potent apoptotic agent against HL-60 cells, Bioorg Med Chem 2004, 45-51,12.
Nyakern et al., Frequent elevation of Akt kinase phosphorylation in blood marrow and peripheral blood mononuclear cells from high-risk myelodysplastic syndrome patients, Leukemia 2006, 230-238, 20.
Ogretman & Hannun, Biologically active sphingolipids in cancer pathogensis and treatment, Nature Rev Cancer 2004, 604-616, 4.
Okada et al., Involvement of N-terminal-extended form of sphingosine kinase 2 in serum-dependent regulation of cell proliferation and apoptosis, JBC 2005, 36318-36325, 280.
Olivera et al., Sphingosine kinase expression increases intracellular sphingosine-1-phosphate and promotes cell growth and survival JBC 1999, 545-558, 147.
Paugh et al., The immunosuppressant FTY720 is phosphorylated by sphingosine kinase type 2, FEBS lett 2003, 189-193, 554.
Pitson et al., Phosphorylation-dependent translocation of sphingosine kinase to the plasma membrane drives its oncogenic signalling, J Exp Med 2005, 49-54, 201.
Anelli et al., Sphingosine kinase 1 is up-regulated during hypoxia in U87MG glioma cells, JBC 2008, 3365-3375, 283.
Barthwal et al., Negative regulation of mixed lineage kinase 3 by protein kinase B/AKT leads to cell survival, JBC 2003, 3897-3902, 278.
Coward et al., Safingol (L-threo-sphinganine) induces autophagy in solid tumor cells through inhibition of PKC and the PI3-kinase pathway, Autophagy 2009, 184-193, 5.
Cuvillier et al., Downregulating sphingosine kinase-1 for cancer therapy, Expert. Opin. Ther. Targets 2008, 1009-1020, 12.
Giannini et al., Patient tumor EGFR and PDGFRA gene amplifications retained in an invasive intracranial xenograft model of glioblastoma multiforme, Neuro-Oncology 2005, 164-176, 7.
Giussani et al., Phosphatidylinositol 3-kinase/AKT pathway regulates the endoplasmic reticulum to golgi traffic of ceramide in glioma cells, JBC 2009, 5088-5096, 284.
Haas-Kogan et al., Protein kinase B (PKB/Akt) activity is elevated in glioblastoma cells due to mutation of the tumor suppressor PTEN/MMAC, Current Biology 1998, 1195-1198, 8.
Hannun and Obeid, Principles of bioactive lipid signalling: lessons from sphingolipids, Nature Reviews Molecular Cell Biology 2008, 139-150, 9.
Kim et al., Akt phosphorylates and negatively regulates apoptosis signal-regulating kinase 1, Molecular and Cellular Biology 2001, 893-901, 21.
Kusner et al., The localization and activity of sphingosine kinase 1 are coordinately regulated with actin cytoskeletal dynamics in macrophages, JBC 2007, 23147-23162, 282.
Lepley et al., The G protein-coupled receptor S1P2 regulates Rho/Rho kinase pathway to inhibit tumor cell migration, Cancer Res. 2005, 3788-3795, 65.
Le Scolan et al., Overexpression of sphingosine kinase 1 is an oncogenic event in erythroleukemic progression, Blood 2005, 1808-1816, 106.
Li et al., Clinical significance of sphingosine kinase-1 expression in human astrocytomas progression and overall patient survival, Clin. Cancer Res. 2008, 6996-7003, 14.
Maceyka et al. Filamin A links sphingosine kinase 1 and sphingosine-1-phosphate receptors 1 at lamellipodia to orchestrate cell migration, Molecular and Cellular Biology 2008, 5687-5697, 28.
Maher et al., Malignant glioma: genetics and biology of a grave matter, Genes Dev. 2001, 1311-1333, 15.

Malchinkhuu et al., Role of p38 mitogen-activated kinase and c-Jun terminal kinase in migration response to lysophosphatidic acid and sphingosine-1-phosphate in glioma cells, Oncogene 2005, 6676-6688, 24.

Mattoon et al., The docking protein Gab1 is the primary mediator of EGF-stimulated activation of the PI-3K/Akt cell survival pathway, BMC Biology 2004, 24-35, 2.

MERRILL et al., Sphingcolipidomics: high-throughput, structure-specific, and quantitative analysis of sphingolipids by liquid tandem mass spectrometry, Methods 2005, 207-224, 36.

Murph and Mills, Targeting the lipids LPA and S1P and their signalling pathways to inhibit tumour progression, Expert Rev Mol Med 2007, 1-18, 9.

Nakamizo et al., Human bone marrow-derived mesenchymal stem cells in the treatment of gliomas, Cancer Res 2005, 3307-3318, 65.

Olivera et al., Sphingosine kinase type 1 induces G12/13-mediated stress fiber formation, yet promotes growth and survival independent of G protein-coupled receptors, JBC 2003, 46452-46460, 278.

Paugh et al., A selective sphingosine kinase 1 inhibitor integrates multiple molecular therapeutic targets in human leukemia, Blood 2008, 1382-1391, 112.

Pchejetski et al., Sphingosine kinase-1 as a chemotherapy sensor in prostate adenocarcinoma cell and mouse models, Cancer Res. 2005, 11667-11675, 65.

Qu et al., Iodophenyl tagged sphingosine derivatives: synthesis and preliminary biological evaluation, Bioorg & Med Chem Lett 2009, 3382-3385, 19.

Radeff-Huang et al., Tumor necrosis factor-alpha-stimulated cell proliferation is mediated through sphingosine kinase-dependent Akt activation and cyclin D expression, JBC 2007, 863-870, 282.

Riboni et al., Ceramide levels are inversely associated with malignant progression of human glial tumors, Glia 2002, 105-113, 39.

Sankala et al., Involvement of sphingosine kinase 2 in p53-independent induction of p21 by the chemotherapeutic drug doxorubicin, Cancer Res. 2007, 10466-10474, 67.

Shida et al., Cross-talk between LPA1 and epidermal growth factor receptors mediates up-regulation of sphingosine kinase 1 to promote gastric cancer cell motility and invasion, Cancer Res. 2008, 6569-6577, 68.

Shida et al., Targeting SphK1 as a new strategy against cancer, Current Drug Targets 2008, 662-673, 9.

Stommel et al., Coactivation of receptor tyrosine kinases affects the response of tumor cells to targeted therapies, Science 2007, 287-290, 318.

Wen et al., Malignant gliomas in adults, N. Engl J. Med. 2008, 492-507, 359.

Van Brocklyn et al., Sphingosine-1-phosphate stimulates human glioma cell proliferation through Gi-coupled receptors: role of ERK MAP kinase and phosphatidylinositol 3-kinase beta, Cancer Lett 2002, 195-204, 181.

Van Brocklyn et al., Sphingosine-1-phosphate stimulates motility and invasiveness of human glioblastoma multiforme cells, Cancer Lett 2003, 53-60, 199.

Van Brocklyn et al., Sphingosine kinase-1 expression correlates with poor survival of patients with glioblastoma multiforme: roles of sphingosine kinase isoforms in growth of glioblastoma cell lines, J Neuropathol Exp Neurol 2005, 695-705, 64.

Xia et al., Opposing effects of ERK and JNK-p38 MAP kinases on apoptosis, Science 1995, 1326-1331, 270.

Yacoub et al., MDA-7 regulates cell growth and radiosensitivity in vitro of primary (non-established) human glioma cells, Cancer Biology & Therapy 2004, 739-751, 3.

Yacoub et al., MDA-7/IL-24 plus radiation enhance survival in animals with intracranial primary human GBM tumors, Cancer Biology & Therapy 2008, 917-933, 7.

Yacoub et al., Regulation of GST-MDA-7 toxicity in human glioblastoma cells by ERBB1, ERK1/2, PI3K, and JNK1-3 pathway signaling, Mol Cancer Ther 2008, 314-329, 7.

Young et al., Roles of sphingosine-1-phosphate (S1P) receptors in malignant behaviour of glioma cells. Differential effects of S1P2 on cell migration and invasiveness, Exp Cell Res. 2007, 1615-1627, 313.

Delgado et al., Inhibitors of sphingolipid metabolism enzymes, Biochimica et Biophysica Acta Biomembranes, 2006, 1957-1977, 1758.

Jeremias et al., Cell death induction by betulinic acid, ceramide and TRAIL in primary glioblastoma multiforme cells, Acta Neurochir (Wien), 2004, 721-729, 146.

Bektas et al., A sphingosine kinase inhibitor induces cell death in temozolomide resistant glioblastoma cells, Cancer Chemother Pharmacol 2009, 1053-1058, 64.

Van Brocklyn, James R., Sphingolipid signaling pathways as potential therapeutic targets in gliomas, Mini-Reviews in Medicinal Chemistry 2007, 984-990, 7.

Wong et al., Synthesis and Evaluation of Sphingosine Analogues as Inhibitors of Sphingosine Kinases, J. Med. Chem. 2009, 3618-3626, 52.

Rahmani et al., Coadministration of histone deacetylase inhibitors and perifosine synergistically induces apoptosis in human leukemia cells through Akt and ERK1/2 inactivation and the generation of ceramide and reactive oxygen species, Cancer Res 2005, 2422-2432, 65.

Rosato et al., The histone deacetylase inhibitor LAQ824 induces human leukocyte cell death through a process involving XIAP down-regulation, oxidative injury, and the acid sphingomyelinase-dependent generation of ceramide, Mol Pharmacol 2006, 216-225, 69.

Rosato et al., Mechanism and functional role of XIAP and Mcl-1 down-regulation in flavopiridol/vorinstat antileukemic interactions, Mol Cancer Ther 2007, 692-702, 6.

Sabbadini, R.A., Targeting sphingosine-1-phosphate for cancer therapy, Br J Cancer 2006, 1131-1135, 95.

Sobue et al., Quantitative RT-PCR analysis of sphingolipid metabolic enzymes in acute leukemia and myelodysplastic syndromes, Leukemia 2006, 2042-2046, 20.

Spiegel et al. Sphingosine-1-phosphate: an enigmatic signalling lipid, Nature Rev Mol Cell Biol. 2003, 397-407,4.

Steelman et al., JAK/STAT, Raf/MEK/ERK, PI3K/Akt and BCR-ABL in cell cycle progression and leukemogenesis, Leukemia 2004, 189-218, 18.

Suguira et al., Ceramide kinase, a novel lipid kinase, JBC 2002, 23294-23300, 277.

Sukocheva et al. Estrogen transactivates EGFR via the sphingosine 1-phosphate receptor Edg-3: the role of sphingosine kinase-1, J Cell Biol 2006, 301-310, 173.

Sullards, et al., Analysis of sphingosine 1-phosphate, ceramides and other bioactive sphingolipids by high-performance liquid chromatography-tandem mass spectrometry, Science STKE 2001, L1.

Swanton et al., Regulators of mitotic arrest and ceramide metabolism are determinants of sensitivity to paclitaxel and other chemotherapeutic drugs, Cancer Cell 2007, 498-512, 11.

Taha et al., Loss of sphingosine kinase-1 activates the intrinsic pathway of programmed cell death: modulation of sphingolipid levels and the induction of apoptosis, FASEB J 2006, 482-484, 20.

Xia et al., Sphingosine kinase interacts with TRAF2 and dissects tumor necrosis factor-alpha signaling, JBC 2002, 7996-8003, 277.

Zhang et al., Bcl-2 interrupts the ceramide-mediated pathway of cell death, PNAS USA 1996, 5325-5328, 93.

* cited by examiner

SEQUENCE LISTING

```
<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gggcaaggcc ttgcagctc                                                  19
```

SPHINGOSINE KINASE TYPE 1 INHIBITORS, COMPOSITIONS AND PROCESSES FOR USING SAME

This invention was made with government support under Grant R01 CA61774 awarded by National Cancer Institute (NCI). The government has certain rights in the invention.

RELATED APPLICATIONS

This application is related to Provisional Application No. 61/048,638, filed Apr. 29, 2008.

FIELD OF THE INVENTION

The invention generally relates to the field of sphingolipids mediation, sphingolipid mediators and sphingokinase inhibitors including particularly Type 1, and the uses of such inhibitors in treatments for cancer, asthma, anaphylaxis, autophagy, central nervous system and others.

All patents, patent applications, patent publications, scientific articles and the like, cited or identified in this application, are hereby incorporated by reference in their entirety in order to describe more fully the state of the art to which the present invention pertains.

BACKGROUND OF THE INVENTION

Sphingosine-1-phosphate (Si P), a potent lipid mediator produced from sphingosine by sphingosine kinases (SphKs), regulates many processes important for cancer progression, including cell growth and survival (Spiegel et al., *Nature Rev Mol Cell Biol.* 4:397-407, 2003). In contrast to S1P, its precursors, sphingosine and ceramide, are associated with growth arrest and induction of apoptosis (Ogretman & Hannun, *Nature Rev Cancer* 4:604-616, 2004). Thus, the balance between these interconvertible sphingolipid metabolites has been viewed as a cellular rheostat determining cell fate (Cuvillier et al., *Nature* 381:800-803, 1996). Numerous studies have shown that perturbations in the S1P/ceramide rheostat are involved in the regulation of resistance to chemotherapy and radiation therapy of neoplastic cells, including those of hematopoietic origin (Ogretman et al., supra.; Hait et al., *Biochim Biophys Acta* 1758:2016-2026. 2006; and Milstien & Spiegel, *Cancer Cell* 9:148-150, 2006).

Two Sphk isoenzymes, SphKI and SphK2, have been described which, while sharing many features (Kohama et al., *J. Biol Chem* 273:23722-23728, 1998; and Liu et al., *J. Biol Chem* 275:19513-19520, 2000) exhibit distinct functions. SphK1 promotes cell growth and survival (Olivera et al., *J Cell Biol* 147:545-558, 1999; Xia et al., *J. Biol Chem* 277: 7996-8003, 2002; Bonhoure et al., *Leukemia* 20:95-102, 2006; and Sukocheva et al., *J Cell Biol* 173:301-310, 2006), whereas SphK2, when overexpressed, has opposite effects (Maceyka et al., *J Biol Chem* 280:37118-37129, 2005; and Okada et al., *J Biol Chem* 280:36318-36325, 2005). SphK1 is a key enzyme that regulates the S1P/ceramide rheostat (Maceyka et al., supra.; Berdyshev et al., *Cell Signal* 18:1779-1792, 2006; and Taha et al., *FASEB J* 20:482484, 2006). Indeed, S1P and SphK1 have long been implicated in resistance of both primary leukemic cells and leukemia cell lines to apoptosis induced by commonly used cytotoxic agents (Cuvillier et al., *Nature,* 2004 supra.; Cuvillier et al., *J. Biol Chem* 273:2910-2916, 1998; Cuvillier et al., *Blood* 98:2828-2836, 2001; and Jendiroba et al., *Leuk Res* 26:301-310, 2002). Non-isozyme specific inhibitors of SphKs, such as L-threo-dihydrosphingosine (safingol) and N,N-dimethylsphingosine (DMS), are cytotoxic to leukemia cells (Jarvis et al., *Mol Pharmacol* 54:844-856, 1998; and Jendiroba et al., 2002, supra.). Interestingly, multi-drug resistant HL-60 myelogenous leukemia cells were more sensitive to DMS than the parental cells (Jendiroba et al., 2002, supra.). Moreover, SphK1 activity was lower in HL-60 cells sensitive to doxorubicin or etoposide than in MDRI- or MRP1-positive HL-60 cells. Enforced expression of SphKI in sensitive HL-60 cells blocked apoptosis whereas downregulation of Sphk1 overcame chemoresistance by inducing mitochondria-dependent apoptosis (Bonhoure et al., 2006, supra.). These observations take on added significance in light of evidence that MDR expression is a strong prognostic indicator in acute myelogenous leukemia (AML) (Filipits et al., *Leukemia* 14:68-76, 2000) and that the MDR phenotype, which commonly arises following treatment of AML with anthracyclines or plant-based alkaloids, is thought to represent an obstacle to successful chemotherapy. In addition, resistance of K562 human chronic myeloid leukemia cells to Imatinib, an inhibitor of Bcr-Abl tyrosine kinase, correlated with expression of SphK1 and generation of S1P, whereas downregulation of SphK1 increased sensitivity to Imatinib-induced apoptosis in resistant cells (Baran et al., *J Biol Chem* 282:10922-10934, 2007). Thus, the development of effective and specific inhibitors of SphK1 might prove useful not only in diminishing levels of pro-survival S1P, but also in potentiating ceramide generation, a process that mediates, at least in part, the pro-apoptotic actions of certain cytotoxic agents (Maggio et al., *Cancer Res* 64:2590-2600, 2004; Rahmani et al., *Cancer Res* 65:2422-2432, 2005; and Rosato et al., *Mol Pharmacol* 69:216-225, 2006).

Sphingosine kinase inhibitors have been described (Kim et al., *Bioorg & Med Chem* 13:3475-3485, 2005; Kono et al., *J. Antibiotics* 53:459-466, 2000; Kono et al., *J. Antibiotics* 53:753-758, 2000; Marsolais & Rosen, *Nature Reviews/Drug Discovery* 8:297-307, 2009; and US 2008/0167352 A1 (Smith et al., published Jul. 10, 2008). None of these publications describe, however, the novel sphingosine kinase Type 1 inhibitors herein.

Here we describe a potent, water-soluble inhibitor of SphK1 (SK1-I) that triggers multiple perturbations in activation of various signaling and survival-related proteins. Sk1-I markedly induced apoptosis in human leukemic cell lines as well as blasts obtained from patients with AML and inhibited growth of AML xenograft tumors. Sk1-I serves as model for other related compounds which are described further below.

SUMMARY OF THE INVENTION

This invention also provides a composition which inhibits sphingosine kinase 1 (SphK1) at least five times greater than it inhibits sphingosine kinase 2 (SphK2) in an in vitro assay that measures sphingosine kinase activity.

The present invention provides a composition comprising the structure

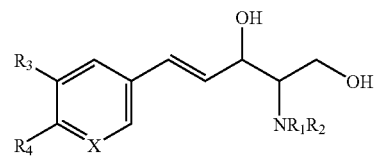

wherein X is C or N and wherein $R_1$, $R_2$, $R_3$, and $R_4$, independently comprise hydrogen, a linear or branched ($C_1$-$C_{18}$)

alkyl group, a substituted linear or branched ($C_1$-$C_{16}$) alkyl group, a cycloalkyl group, a substituted cycloalkyl group, a heterocyclic group, a substituted heterocyclic group, an aryl alkyl group, a substituted aryl alkyl group, a heteroarylalkyl group, a substituted heteroarylalkyl group, an alkoxy group, a substituted alkoxy group, an alkene group, a substituted alkene group, an alkyne group, an acyl group, a sulfide, or an ether group, and wherein $R^1$ and $R^2$, $R^3$ and $R^4$ may independently be fused together to form one or more rings, or any combination of the foregoing.

The compositions of this invention are useful in a number of applications or settings including killing or damaging cancer cells, inducing apoptosis, inhibiting growth, metastasis and development of chemoresistance in cancer cells, leukemia, increasing the effectiveness of anti-cancer agents, attenuating immune reactivity, inhibiting survival signaling in cancer cells, and reducing symptoms of multiple sclerosis.

DESCRIPTION OF THE INVENTION

Figure 1A:
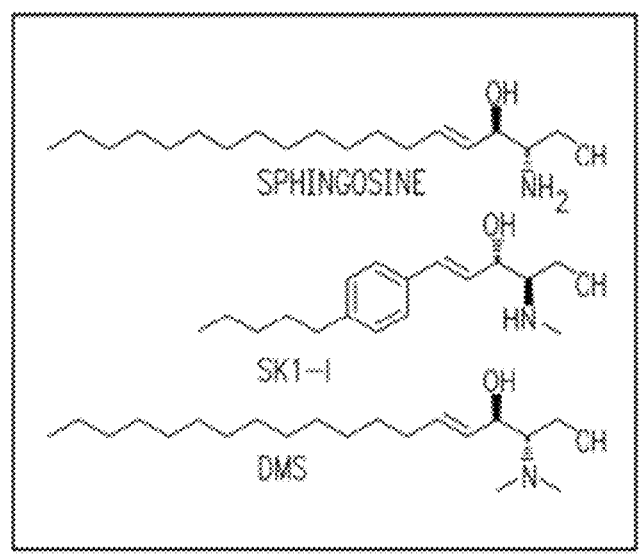
FIG. 1A shows the structure for SK1-I (BML-258).
Figure 1B:
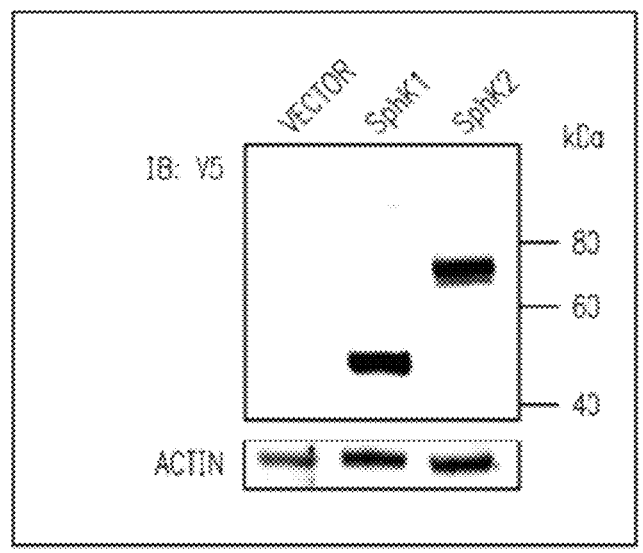
FIG. 1B-F are results showing the effects of SK1-I on recombinant SphK1 and SphK2.
Figure 1C:
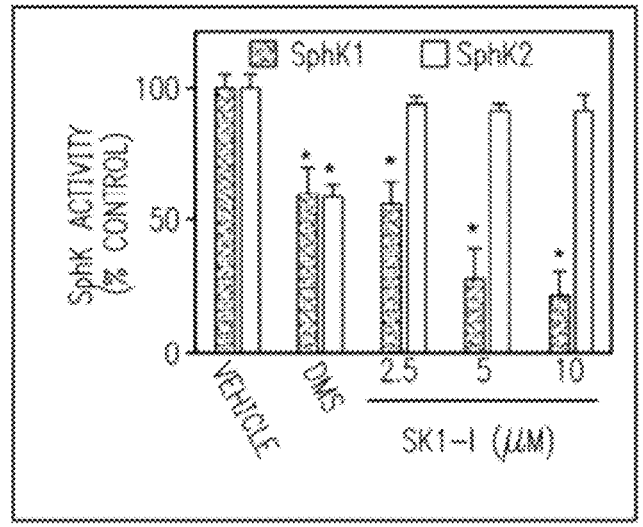
Figure 1D:
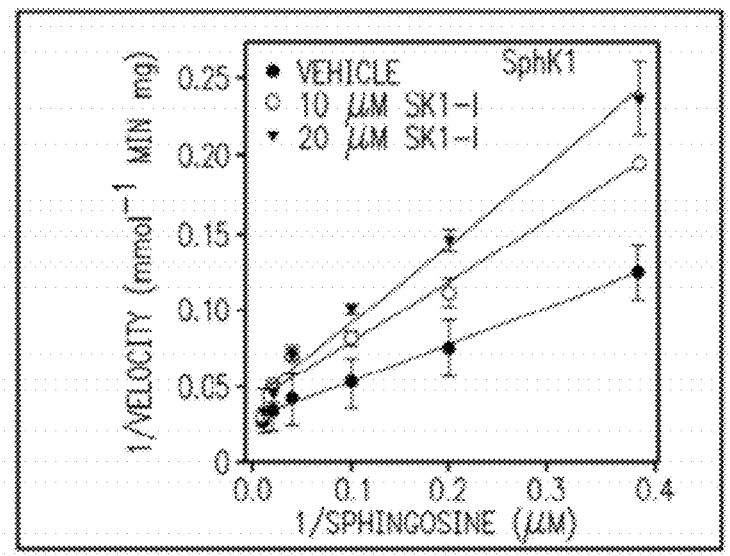
Figure 1E:
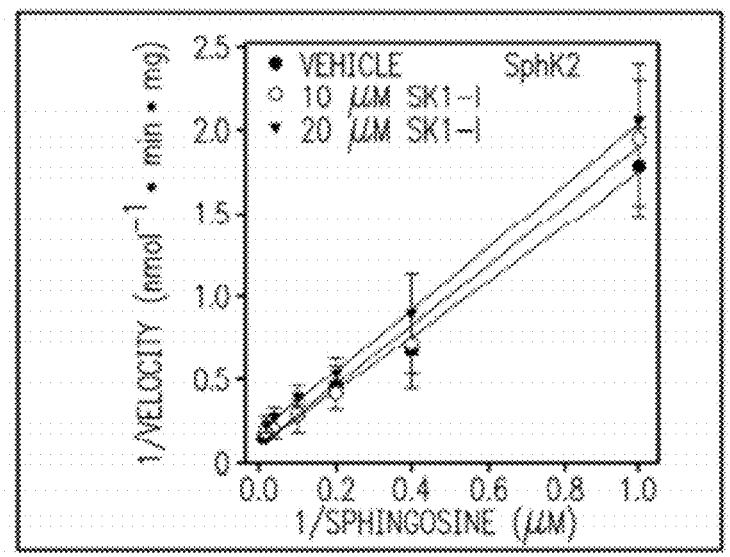

This invention provides a composition comprising the structure

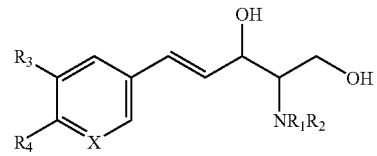

wherein X is C or N and wherein $R_1$, $R_2$, $R_3$, and $R_4$, independently comprise hydrogen, a linear or branched ($C_1$-$C_{18}$) alkyl group, a substituted linear or branched ($C_1$-$C_{16}$) alkyl group, a cycloalkyl group, a substituted cycloalkyl group, a heterocyclic group, a substituted heterocyclic group, an aryl alkyl group, a substituted aryl alkyl group, a heteroarylalkyl group, a substituted heteroarylalkyl group, an alkoxy group, a substituted alkoxy group, an alkene group, a substituted alkene group, an alkyne group, an acyl group, a sulfide, or an ether group, and wherein $R^1$ and $R^2$, $R^3$ and $R^4$ may independently be fused together to form one or more rings, or any combination of the foregoing.

This invention also provides a composition comprising the structure

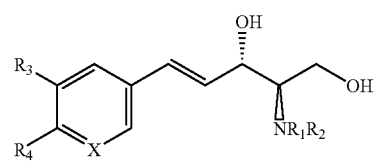

This invention also provides a composition having the structure

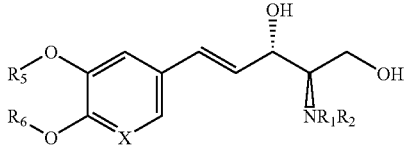

wherein $R_5$ and $R_6$ independently comprise a linear or branched ($C_1$-$C_{18}$) alkyl group, a substituted linear or branched ($C_1$-$C_{16}$) alkyl group, a cycloalkyl group, a substituted cycloalkyl group, a heterocyclic group, a substituted heterocyclic group, an aryl alkyl group, a substituted aryl alkyl group, a heteroarylalkyl group, a substituted heteroarylalkyl group, an alkoxy group, a substituted alkoxy group, an alkene group, a substituted alkene group, an alkyne group, an acyl group, a sulfide, an ether group or any combination of the foregoing.

Also provided by this invention is a further composition wherein $R_5$ and $R_6$ are joined together to form a ring, the composition comprising the structure

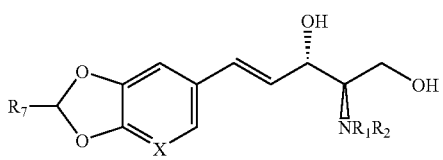

wherein $R_7$ comprises hydrogen, a linear or branched ($C_1$-$C_{18}$) alkyl group, a substituted linear or branched ($C_1$-$C_{16}$) alkyl group, a cycloalkyl group, a substituted cycloalkyl group, a heterocyclic group, a substituted heterocyclic group, an aryl alkyl group, a substituted aryl alkyl group, a heteroarylalkyl group, a substituted heteroarylalkyl group, an alkoxy group, a substituted alkoxy group, an alkene group, a substituted alkene group, an alkyne group, an acyl group, a sulfide, an ether group or any combination of the foregoing.

In another embodiment, a composition is provided wherein $R_1$ is H and $R_2$ is $CH_3$. Yet in another composition, $R_3$ or $R_4$ is a sulfide, $SR_5$, wherein $R_5$ comprises hydrogen, a linear or branched ($C_1$-$C_{18}$) alkyl group, a substituted linear or branched ($C_1$-$C_{16}$) alkyl group, a cycloalkyl group, a substituted cycloalkyl group, a heterocyclic group, a substituted heterocyclic group, an aryl alkyl group, a substituted aryl alkyl group, a heteroarylalkyl group, a substituted heteroarylalkyl group, an alkoxy group, a substituted alkoxy group, an alkene group, a substituted alkene group, an alkyne group, an acyl group, a sulfide, an ether group or any combination of the foregoing.

Another composition is provided wherein $SR_5$ has the structure:

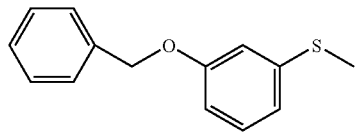 [SMILES: CSc1cccc(OCc2ccccc2)c1]

Still in another composition X is C, $R_1$ and $R_3$ are H and $R_4$ is $SR_5$, the composition having the structure:

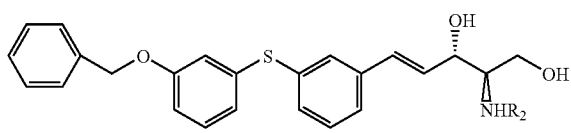

$R_2$ can be $CH_3$. X can be C, $R_1$ and $R_4$ are H and $R_3$ is $SR_5$, the composition having the structure:

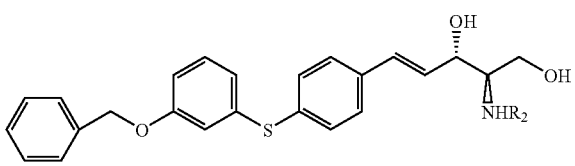

In the above compositions, $R_2$ can be $CH_3$ and $R_3$ can be H.

In another embodiment, X is C, $R_1$ is H, $R_2$ is $CH_3$, and $R_4$ is $(CH_2)_4CH_3$, the compound having the structure

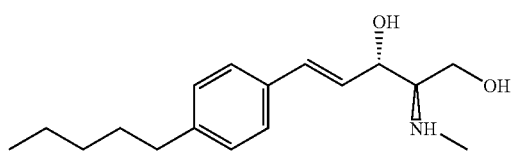 [SMILES: CCCCCc1ccc(/C=C/[C@H](O)[C@@H](CO)NC)cc1]

The terminal carbon of $R_4$ can be substituted by one or more halides, where the halide is a bromine, chloride or fluoride In another embodiment, the composition has the structure:

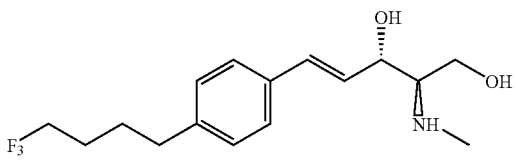

$R_4$ can be H, $R_2$ is a methyl group, $R_1$ is hydrogen or a methyl group.

Also $R_1$ and $R_2$ can be fused together to from a substituted or unsubstituted ring.

In another embodiment, this invention provides a composition having the structure

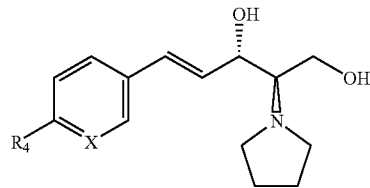

X can be C.

Another composition has the structure

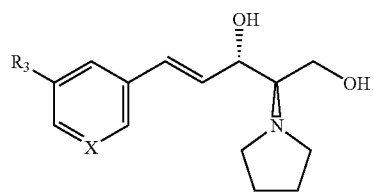

Here, X is C. Also, $R_4$ can be an ether, the compound having the structure:

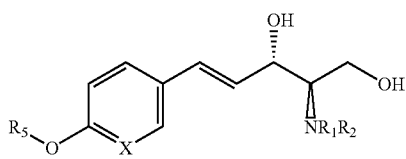

wherein $R_5$ comprises a linear or branched ($C_1$-$C_{18}$) alkyl group, a substituted linear or branched ($C_1$-$C_{16}$) alkyl group, a cycloalkyl group, a substituted cycloalkyl group, a heterocyclic group, a substituted heterocyclic group, an aryl alkyl group, a substituted aryl alkyl group, a heteroarylalkyl group, a substituted heteroarylalkyl group, an alkoxy group, a substituted alkoxy group, an alkene group, a substituted alkene group, an alkyne group, an acyl group, a sulfide, an ether group or any combination of the foregoing.

In further embodiments, X can be C, $R_1$ is H and $R_2$ is $CH_3$.

A number of useful processes are provided with the above-described compositions.

These include a process of killing or damaging cancer cells, comprising the step of exposing said cancer cells to the composition(s) in an amount sufficient to kill or damage said cancer cells. Such cancer cells comprise leukemia cells, breast cancer cells, prostate cancer cells, pancreatic cancer cells, glioma cancer cells, colon cancer cells, lung cancer cells, ovarian cancer cells, melanoma cells, or renal cancer cells, and combinations thereof.

Another process provided by this invention causes cancer cells to undergo apoptosis, and comprises the step of exposing the cancer cells to the composition(s) in an amount sufficient to cause said cancer cells to undergo apoptosis. Again, such cancer cells comprise leukemia cells, breast cancer cells, prostate cancer cells, pancreatic cancer cells, glioma cancer cells, colon cancer cells, lung cancer cells, ovarian cancer cells, melanoma cells, or renal cancer cells, and combinations thereof.

This invention also provides a process for inhibiting growth, metastasis and development of chemoresistance in cancer cells, comprising the step of exposing the cancer cells to the composition(s) in an amount sufficient to inhibition of growth, metastasis and development of chemoresistance in said cancer cells. Again, the cancer cells comprise leukemia cells, breast cancer cells, prostate cancer cells, pancreatic cancer cells, glioma cancer cells, colon cancer cells, lung cancer cells, ovarian cancer cells, melanoma cells, or renal cancer cells, and combinations thereof.

Another process is for treating or reducing symptoms of leukemia in a patient in need thereof, comprising the step of administering the composition(s) to said patient in an amount sufficient to treat or reduce symptoms of leukemia in said patient.

Yet another process is for increasing the ability of an anticancer agent to kill cancer cells in a patient in need thereof, comprising the step of administering to the patient the anticancer agent; and the composition(s), the composition being administered in an amount sufficient to increase the ability of the anticancer agent to kill the cancer cells in the patient. The cancer cells can comprise leukemia cells, breast cancer cells, prostate cancer cells, pancreatic cancer cells, glioma cancer cells, colon cancer cells, lung cancer cells, ovarian cancer cells, melanoma cells, or renal cancer cells, and combinations thereof.

Also provided is a process of attenuating immune reactivity in a patient in need thereof, comprising the step of administering the composition(s) to the patient in an amount sufficient to attenuate immune reactivity in the patient. In further embodiments, the attenuation of immune reactivity is carried out by attenuation of mast cell functions. Also, the attenuation of immune reactivity can be directed to reducing symptoms of asthma in a patient in need thereof. The attenuation of immune reactivity can also be directed to reducing symptoms of anaphylactic shock or it can be directed to reducing symptoms of autoimmune disease.

Yet another process that is provided is for inhibiting survival signaling in cancerous cells, comprising the step of administering to the cancerous cells the composition of claim 1 in an amount sufficient to inhibit the survival signaling. In another embodiment, the inhibition of survival signaling is carried out by attenuation of phosphorylation of Akt or ERK1/2 or both.

Yet provided is another process of reducing the symptoms of multiple sclerosis in a patient in need thereof, comprising the step of administering the composition(s) to the patient in an amount sufficient to reduce symptoms of multiple sclerosis in the patient.

This invention also provides a composition which inhibits sphingosine kinase 1 (SphK1) at least five times greater than it inhibits sphingosine kinase 2 (SphK2) in an in vitro assay that measures sphingosine kinase activity. SphK1 can also be inhibited at least ten times greater than the inhibition of said SphK2. Inhibition in the in vitro assay is measured at a 10 µM concentration. The inhibition in the in vitro assay can also be measured at a concentration that gives fifty percent (50%) inhibition of SphK1.

The last-mentioned compositions are also useful in a number of applications or settings. These include a process of killing or damaging cancer cells, comprising the step of exposing the cancer cells to the last-described composition(s) in an amount sufficient to kill or damage the cancer cells. The cancer cells can comprise leukemia cells, breast cancer cells, prostate cancer cells, pancreatic cancer cells, glioma cancer cells, colon cancer cells, lung cancer cells, ovarian cancer cells, melanoma cells, or renal cancer cells, and combinations thereof.

In another embodiment, the last-described composition is useful in a process of causing cancer cells to undergo apoptosis, comprising the step of exposing the cancer cells to that composition in an amount sufficient to cause the cancer cells to undergo apoptosis. Again, the cancer cells can comprise leukemia cells, breast cancer cells, prostate cancer cells, pancreatic cancer cells, glioma cancer cells, colon cancer cells, lung cancer cells, ovarian cancer cells, melanoma cells, or renal cancer cells, and combinations thereof.

In another process involving the last-described compositions, this invention provides a process for inhibiting growth, metastasis and development of chemoresistance in cancer cells, comprising the step of exposing the cancer cells to the composition(s) in an amount sufficient to inhibition of growth, metastasis and development of chemoresistance in the cancer cells.

The cancer cells can comprise leukemia cells, breast cancer cells, prostate cancer cells, pancreatic cancer cells, glioma cancer cells, colon cancer cells, lung cancer cells, ovarian cancer cells, melanoma cells, or renal cancer cells, and combinations thereof.

A process of treating or reducing symptoms of leukemia in a patient in need thereof, comprising the step of administering the last-described composition(s) to the patient in an amount sufficient to treat or reduce symptoms of leukemia in the patient.

In another embodiment, there is provided a process of increasing the ability of an anticancer agent to kill cancer cells in a patient in need thereof, comprising the step of administering to the patient the anticancer agent; and the last-described compositions, the composition being administered in an amount sufficient to increase the ability of the anticancer agent to kill cancer cells in the patient. The cancer cells can comprise leukemia cells, breast cancer cells, prostate cancer cells, pancreatic cancer cells, glioma cancer cells, colon cancer cells, lung cancer cells, ovarian cancer cells, melanoma cells, or renal cancer cells, and combinations thereof.

Also provided is a process of attenuating immune reactivity in a patient in need thereof, comprising the step of administering the last-described composition(s) to the patient in an amount sufficient to attenuate immune reactivity in the patient. In other embodiments, attenuation of immune reactivity is carried out by attenuation of mast cell functions. The attenuation of immune reactivity can be directed to reducing symptoms of asthma in a patient in need thereof, to reducing symptoms of anaphylactic shock, or to reducing symptoms of autoimmune disease.

In another embodiment, this invention provides a process for inhibiting survival signaling in cancerous cells, comprising the step of administering to the cancerous cells the last-described composition(s) in an amount sufficient to inhibit survival signaling. Inhibition of survival signaling can be carried out by attenuation of phosphorylation of Akt or ERK1/2 or both.

Another process provided by this invention is for reducing the symptoms of multiple sclerosis in a patient in need thereof, comprising the step of administering the last-described composition(s) to the patient in an amount sufficient to reduce symptoms of multiple sclerosis in the patient.

It should recognized that any of the compositions of the present invention which are described herein can be formulated into compositions in oligomeric or polymeric form.

Also, the present compositions can be formulated into pharmaceutical compositions which have been combined with conventional ingredients using processes known to those skilled in the art. These compositions can be formulated as tablets, pills, capsules, liquids, gels, syrups, slurries, suspensions and the like for ingestion by the patient.

The following examples are offered by way of illustration and not by way of limitation to the present invention.

DESCRIPTION OF THE PREFERRED EMBODIMENTS

Example 1

Synthesis of BML-258

The compound described and used below, BML-258, was synthesized according to the following protocol and procedures.

BML-258 Synthetic Protocol

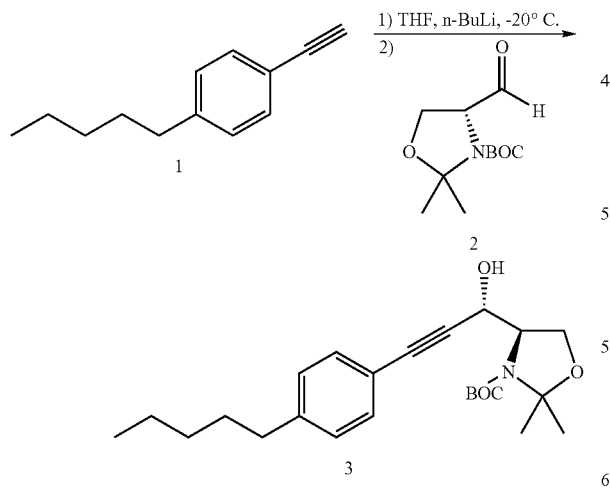

To 4-n-pentylphenylacetylene 1 (3.343 g, 0.01776 mol) in 65 mL dry THF at −20° C. under an atmosphere of $N_2$ was added n-BuLi (10.2 mL of 1.6M in hexanes, 0.01628 mol) dropwise. The reaction mixture was stirred at −20° C. for 2 hours. Methyl (R)-(+)-3-(t-butoxycarbonyl)-2,2-dimethyl-4-oxazolidinecarboxylate 2 (3.393 g, 0.01480 mol) in 25 mL dry THF was added via cannula/$N_2$. The reaction was stirred overnight at −20° C. overnight. TLC (20% Ethyl acetate/hexanes) indicated completeness of reaction. The mixture was diluted with $Et_2O$ and carefully washed with water and brine. Flash column chromatography (12% Ethyl acetate/hexanes, silica gel) yielded 4.50 g (73%) of a mixture of erythro and threo products. Preparative HPLC (Dynamax Si, 15% Ethyl acetate/hexanes, 260 nm) yielded 3.71 g erythro 3 and 0.49 g threo. 1H NMR(CDCl$_3$) erythro: 7.34-7.32 (d, 2H), 7.12-7.09 (d, 2H), 5.19-5.16 (d, 1H), 4.73-4.70 (d, 1H), 4.26-3.96 (m, 3H), 2.61-2.56 (t, 2H), 1.62 (s, 3H), 1.60-1.50 (m, 2H), 1.54 (s, 3H), 1.50 (s, 9H), 1.34-1.27 (m, 4H), 0.91-0.86 (t, 3H).

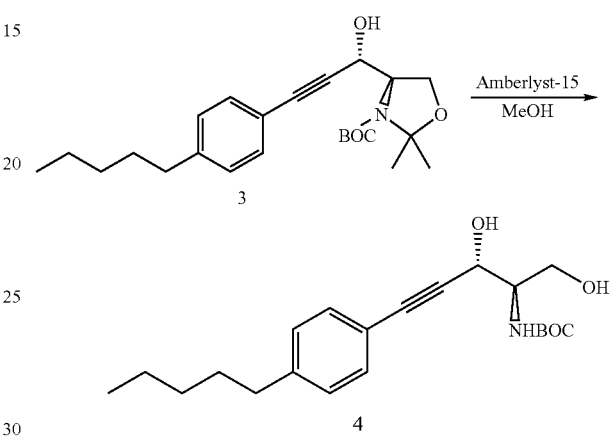

To oxazolidine 3 (3.48 g, 0.00814 mol) in 100 mL MeOH was added Amberlyst-15 (200 mg). The reaction was stirred overnight at room temperature. TLC (30% Ethyl acetate/hexanes) indicated completeness of reaction. The mixture was filtered and flash chromatographed (5% MeOH/methylene chloride, silica gel) to give 2.44 g (79%) of aminoalcohol 4. 1H NMR(CDCl$_3$): 7.34-7.32 (d, 2H), 7.12-7.09 (d, 2H), 5.45-5.38 (d, 1H), 4.88-4.82 (m, 1H), 4.25-4.19 (m, 1H), 3.91-3.80 (m, 2H), 3.26-3.23 (d, 1H), 2.61-2.56 (t, 2H), 1.63-1.54 (m, 2H), 1.49 (s, 9H), 1.35-1.26 (m, 4H), 0.91-0.86 (t, 3H).

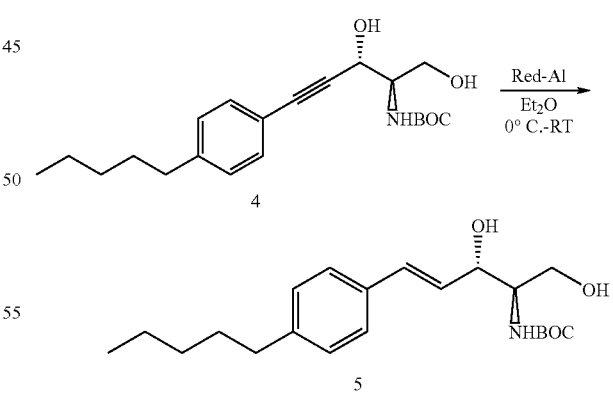

To alkyne 4 (2.44 g, 0.00646 mol) in 125 mL dry $Et_2O$ at 0° C. under an atmosphere of $N_2$ was added Red-Al (9.85 mL of 65 wt % in toluene, 0.03232 mol) dropwise. The reaction was allowed to warm to room temperature following the addition and was stirred for 36 hours. TLC (40% Ethyl acetate/hexanes) indicated completeness of reaction. The reaction was cooled to 0° C. and carefully quenched with 15% NaOH solution. This mixture was stirred vigorously until both layers were clear (45 min). The layers were separated and the aqueous layer extracted with chloroform (3×). The combined organic layers were washed with 15% NaOH, water and brine. Flash chromatography (gradient of 5% MeOH/methylene chloride to 20% MeOH/methylene chloride+1% NH$_4$OH, silica gel) yielded 1.76 g (72%) of trans alkene 5.

1H NMR(CDCl$_3$): 7.31-7.29 (d, 2H), 7.15-7.12 (d, 2H), 6.70-6.65 (d, 1H, J=16 Hz), 6.26-6.18 (dd, 1H, J=16 Hz), 5.35-5.32 (d, 1H), 4.55-4.49 (m, 1H), 4.03-3.96 (m, 1H), 3.80-3.68 (m, 2H), 2.83-2.79 (d, 1H), 2.61-2.56 (t, 2H), 1.65-1.55 (m, 2H), 1.44 (s, 9H), 1.34-1.25 (m, 4H), 0.91-0.86 (t, 3H).

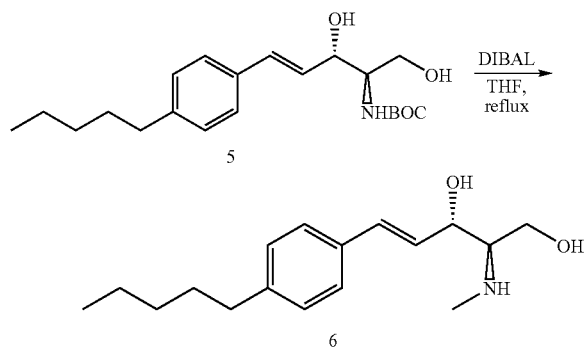

To BOC-alkene 5 (0.350 g, 0.00092 mol) in 20 mL dry THF under an atmosphere of N$_2$ was carefully added DIBAL (9.22 mL of 1M in THF, 0.00922 mol) at room temperature. Following the addition, the reaction was brought to reflux. After 24 hours of reflux, the mixture was cooled to room temperature and an additional 5.0 mL DIBAL solution (0.00500 mol) was added. Reflux was resumed for another 24 hours. The reaction was cooled to 0° C. and carefully quenched with water (0.60 mL), 15% NaOH (0.60 mL) and water again (1.50 mL). THF (50 mL) was added and the mixture stirred vigorously for 15 minutes. Na$_2$SO$_4$ (2 g) and celite (2 g) were then added and stirring was continued for 30 minutes while warming to room temperature. The mixture was filtered and the filter cake extracted with copious THF. Flash chromatography (gradient of 2% MeOH/methylene chloride to 10% MeOH/methylene chloride+0.75% NH$_4$OH) yielded 0.187 g (73%) of amine 6. 1H NMR(CDCl$_3$): 7.31-7.29 (d, 2H), 7.15-7.12 (d, 2H), 6.68-6.63 (d, 1H, J=16 Hz), 6.22-6.14 (dd, 1H, J=16 Hz), 4.51-4.47 (m, 1H), 3.80-3.74 (m, 3H), 2.61-2.56 (t, 2H), 2.50 (s, 3H), 2.40-2.10 (broad, 2H), 1.65-1.55 (m, 2H), 1.34-1.25 (m, 4H), 0.91-0.86 (t, 3H). HRMS(MH+). Calc.—278.2120. Found—278.2119.

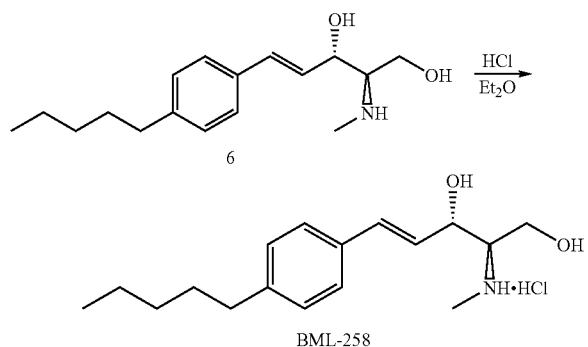

To amine 6 (0.335 g, 0.00121 mol) in 15 mL dry Et$_2$O at 0° C. was added 3.0 mL of 1M HCl/Et$_2$O. A white precipitate formed immediately. After stirring for 15 minutes at room temperature, the precipitate was filtered and washed with Et$_2$O to give 0.325 g (89%) of BML-258. 1H NMR(DMSO): 8.75-8.50 (bd, 2H), 7.38-7.34 (d, 2H), 7.19-7.15 (d, 2H), 6.65-6.60 (d, 1H, J=16 Hz), 6.30-6.22 (dd, 1H, J=16 Hz), 5.84-5.82 (m, 1H), 5.30-5.25 (m, 1H), 4.60-4.54 (m, 1H), 3.76-3.72 (m, 2H), 3.18-3.10 (m, 1H), 2.64 (s, 3H), 2.56-2.50 (t, 2H), 1.60-1.50 (m, 2H), 1.34-1.23 (m, 4H), 0.90-0.85 (t, 3H).

SKI-I, (2R,3S,4E)-N-methyl-5-(4'-pentylphenyl)-2-aminopent-4-ene-1,3-diol (BML-258), was synthesized by BIOMOL International (Plymouth Meeting, Pa.) as described in Example 1. Sphingosine and N,N-dimethylsphingosine were obtained from BIOMOL. [γ-$^{32}$P]ATP (3000 Ci/mmol) was purchased from Perkin Elmer (Boston, Mass.). Boc-D-FMK (BOC), Z-VAD-FMK (ZVAD) and etoposide were from EMD Biosciences (San Diego, Calif.). Terminal deoxynucleotidyl transferase Br-dUTP nick end labeling (TUNEL) kit for flow cytometry was from Sigma Aldrich (St. Louis, Mo.). TUNEL kit for immunohistochemistry was from Roche Applied Science (Indianapolis, Ind.). FITC4 labeled annexin V/propidium iodide staining kit for apoptosis was from BD Biosciences (San Jose, Calif.).

Cells and Cell Culture

U937 human histiocytic leukemia and Jurkat acute T-cell leukemia cells were obtained from American Type Culture Collection (Manassas, Va.). Cells were cultured and maintained in logarithmic growth phase in RPMI 1640 medium supplemented with L-glutamate, penicillin, streptomycin, and 10% fetal bovine serum (Invitrogen, Carlsbad, Calif.) (Dai et al., Cancer Res 61:5106-5115, 2001) unless indicated otherwise. U937 cells stably overexpressing Bcl-2, Bcl-xL, constitutively active Akt (Myc-tagged myristoylated Akt), and their empty-vector counterparts were obtained and cultured in the presence of the appropriate selection antibiotics exactly as described (Rahmani et al., 2005, supra.).

Leukemic blasts were obtained with informed consent from two AML patients undergoing routine diagnostic aspirations with approval from the Institutional Review Board of Virginia Commonwealth University. Informed consent was provided according to the Declaration of Helsinki. The characterization of the two patient samples was as follows:

Patient #1: FAB sub-type M2, no known fusion or mutant proteins, no known chromosome abnormalities.

Patient #2: FAB sub-type M4, no known fusion or mutant proteins, inversion of chromosome 16.

Samples, which contained 85% blasts in each case, were separated by centrifugation over Ficoll/Hypaque (specific gravity 1.077-1.081; Sigma, St Louis, Mo., USA) at 400×g at room temperature. The interface layer, containing primarily blasts, was removed using a sterile Pasteur pipette, and resuspended in medium containing 10% FBS. Cells exhibited>95% viability by trypan blue exclusion and were cultured as described above. Peripheral blood mononuclear leukocytes were isolated similarly from healthy donors.

RNA Interference

U937 cells were transfected with 100 pmol RNAi oligonucleotides targeted to SphK1 (sequence targeted: GGGCAAGGCCTTGCAGCTC (SEQ ID NO: 1)) and non-targeting control siRNA (nonspecific random sequence) obtained from Qiagen (Valencia, Calif.). Transfections were performed with the Amaxa Nucleofector (program V-001) with Cell Line Nucleofector Kit V (Amaxa GmbH, Cologne, Germany) according to the manufacturer's instructions.

Expression and Activity of Sphingosine Kinases

HEK 293 cells were cultured in DMEM containing 10% fetal bovine serum and transfected with V5-His-pcDNA3.1 vector (Invitrogen), V5-His-tagged human SphK1, or V5-His-tagged human SphK2 using Lipofectamine PLUS (Invitrogen) as previously described (Paugh et al., *FEBS Lett* 554:189-193, 2003). Cells were then cultured for 2 days, lysed by freeze-thawing, and SphK1 activity was determined with [$\gamma$-$^{32}$P]ATP (10 pCi, 1 mM, containing 10 mM MgCl$_2$) and sphirigosine in 0.25% Triton X-100, which inhibits SphK2 (Hait et al., *J Biol Chem* 280:29462-29469, 2005). SphK2 activity was determined with sphingosine added as a complex with 4 mg/ml BSA in the presence of 1 M KCl, conditions in which SphK2 activity is optimal and SphK1 strongly inhibited (Hait et al., *J Biol Chem*, 2005, supra.). Labeled SiP was extracted and separated by TLC on silica gel G60 with chloroform/acetone/methanol/acetic acid/H$_2$O (10: 4:3:2:1. v/v) as solvent. Radioactive bands corresponding to S1P were quantified with a FX Molecular Imager (Bio-Rad, Hercules, Calif.). SphK specific activity is expressed as pmol S1P formed per min per mg protein.

Western Blot Analysis

Cells were resuspended in cell lysis buffer (50 mM Tris pH 7.5, 150 mM NaCl, 1% Nonidet P40, 0.5% sodium deoxycholate, 1 mM PMSF, 5 µg/ml leupeptin, 5 µg/ml aprotinin, 1 mM DTT). Equal amounts of protein (60 µg) were separated by 10% SDS-PAGE and then transblotted to nitrocellulose. Blots were incubated with primary antibodies (1:1000) overnight in Tris-buffered saline (TBS) containing 5% non-fat dry milk and 0.1% Tween 20 followed by anti-rabbit HRP-conjugated IgG (1:10,000, Jackson Immunoresearch Laboratories). Immunocomplexes were visualized by enhanced chemiluminescence (Pierce) with Kodak or Phenix Research Products X-ray film. Westerns were quantitated using AlphaEaseFC 4.0.0 software from Alpha Innotech Corporation (San Leandro, Calif.).

The following were used as primary antibodies: phospho-p44/42 MAP kinase (Thr202/Tyr204) antibody, phospho-p38 MAP kinase (Thr180/Tyr182) antibody (Cell Signaling, Beverly, Mass., USA), phospho-JNK (Thr183/Tyr185) antibody, Bcl-xS/L antibody (S-18, Santa Cruz, Santa Cruz, Calif.), anti-human Bcl-2 (Dako, Carpinteria, Calif.), Mcl-1 antibody, anti-caspase-3, and anti-caspase-9 (Pharmingen), and anti-PARP (Biomol).

Protein Kinase Profiling

Effects of SK1-I on the activity of various protein kinases was assessed by SelectScreen™ Kinase Profiling (Invitrogen Drug Discovery Solutions, Madison, Wis.). Briefly, assays were performed in 384-well plates using a fluorescence resonance energy transfer (FRET)-based kinase assay system with peptide substrates containing two fluorophores that make up a FRET pair, in the absence or presence of 5 µM SK1-I and at an ATP concentration of $Km_{app}$ for each protein kinase. The development reagent contains a protease that specifically digests non-phosphorylated peptide and produces a fluorescent signal. Coumarin fluorescence and the fluorescein FRET signal were monitored at 445 nm and 520 nm, respectively. The coumarin emission excites fluorescein by FRET in the uncleaved (phosphorylated) substrate peptide only.

Reactions containing unphosphorylated peptide and kinase in the absence of ATP and stoichiometrically phosphorylated peptide served as 0% and 100% phosphorylation controls, respectively. Raw fluorescence values were corrected for background. Reaction endpoints were calculated as emission ratios of coumarin fluorescence divided by the fluorescein FRET signal. These ratios were then normalized to the ratio obtained with the 100% phosphorylation control.

Annexin V/PI Assays for Apoptosis

Cells were stained with annexin V-fluorescein isothiocyanate and propidium iodide (PI) and then evaluated for apoptosis by flow cytometry according to the manufacturer's protocol (BD PharMingen, San Diego, Calif.). Briefly, $10^6$ cells were washed twice with phosphate-buffered saline (PBS) and stained with 5 µl of annexin V-fluorescein isothiocyanate and 5 µl of P1 (50 µg/ml) in buffer contaning 10 mM HEPES, pH 7.4, 140 mM NaOH, and 2.5 mM CaCl$_2$ for 15 min at room temperature in the dark. The apoptotic cells were determined using a Coulter Epics-XL-MCL cytofluorometer with the EXPO32 Flow Cytometry analytic program (Beckman Coulter, Fullerton, Calif.). The percentages in the lower right quadrant correspond to early apoptotic cells (annexin V positive), whereas percentages in the upper right quadrant correspond to late apoptotic cells (annexin V and P1 positive).

DNA Strand Break Detection By TUNEL Assay

Cells ($10^6$) were fixed with 1% (w/v) paraformaldehyde on ice for 15 min, washed twice with PBS, and permeablized in 70% ethanol on ice for 30 minutes. Cells were washed and resuspended in a DNA labeling solution containing terminal deoxyribonucleotide transferase and bromodeoxyuridine (BrdU) and incubated at 37° C. for 1 h according to the manufacturers instructions (Sigma). Cells were then incubated with anti-BrdU-fluorescein antibody in the dark for 30 mm at room temperature and analyzed using a Coulter Epics-XL-MCL cytofluorometer with the EXPO32 Flow Cytometry analytic program (Beckman Coulter).

Mass Spectrometric Analysis of Sphingolipids and Metabolites

Cells were washed extensively with cold PBS and pelleted by centrifugation at 2000×g for 10 min. An aliquot of cells was taken for DNA and protein measurements. To the rest, internal standards were added (0.5 nmol each C12-SM, C12-Cer, C12-GlcCer, C12-LacCer, C17-sphingosine, C17-sphinganine, C17-sphingosine 1-phosphate, C17-sphinganine-1-phosphate, and C12-Cer-phosphate, Avanti Polar Lipids, Alabaster, Ala.), lipids extracted, and individual ceramide acyl chain species quantified by liquid chromatography, electrospray ionization-tandem mass spectrometry (ESI-MS/MS, 4000 QTRAP, Applied Biosystems) as described previously (Sullards et al., *Science STKE* 2001:L1, 2001).

Xenograft Tumor Model

All experiments involving animals were approved by the VCU IACUC. U937 cells ($2 \times 10^6$ suspended in 100 µl of sterile PBS) were injected into two sites on both flanks of 6 week-old CB17 SCID/beige mice (Taconic Farms, Germantown, N.Y.) and allowed to grow to palpable tumors for 7 days. When tumors reached a volume of 50-100 mm$^3$, animals were randomly assigned to two groups that were injected intraperitoneally with 200 µl of saline or SK1-I (20 mg/kg) on 7 consecutive days. Tumor measurements were made daily with calipers, and tumor volume was calculated using the formula: ($\pi \times$[length in millimeters]$\times$[width in millimeters]$^2$)/6. At the end of the experiment, the animals were killed and the tumors removed, fixed in formalin and embedded in paraffin or frozen in liquid nitrogen. Formalin fixed sections were stained with hematoxylin-eosin, or with antibodies against Ki-67 (Novocastra, Newcastle, UK). Antibody binding was detected by immunohistochemistry and peroxidase-conjugated species-specific secondary antibodies and visualized with 3,3-diaminobenzidine. Paraffin sections were dewaxed, rehydrated, and proteinase K treated prior to permeabilization. Frozen sections were stained with a fluorescein TUNEL labeling kit followed by counterstaining with DAPI. Slides were analyzed by fluorescence microscopy.

Statistical Analysis

Experiments were repeated at least three times with consistent results. For each experiment, data from triplicate samples were calculated and expressed as the mean±S.D. The significance of differences between experimental conditions was determined using the Student's t test for unpaired observations.

Results

SK1-I is a Potent and Selective Inhibitor of SphKI But Not SphK2

Currently, no structural information is available for SphKs to allow use of computational docking methods for the rational design of inhibitors. Therefore, an alternative approach is to utilize information obtained from inhibitor studies to design more potent and selective inhibitors. Various chemically synthesized short-chain sphingosine and dihydro-sphingosine analogs have previously been investigated as inhibitors of SphK (Edsall et al., *Biochemistry* 37:12892-12898, 1998; De Jonghe et al., *Bioorg Med Chem Lett* 9:3175-4180, 1999; Johnson et al., *J. Pharmacol Exp* 309:452-461, 2004; and Niiro et al., *Bioorg Med Chem* 12:45-51, 2004). It was found that replacement of the alkyl chain with a phenyl ring or substituting fluorine for the 3-hydroxyl group yielded potent SphK inhibitors. Moreover, analogs with a 4,5-trans double bond were generally superior inhibitors (Johnson et al., *J Pharmacol Exp*, 2004, supra.). Based on these earlier observations, we synthesized (2R,3S,4E)-N-methyl-5-(4'-pentylphenyl)-2-aminopent-4-ene-1,3-diol (FIG. 1A) and examined its effects on recombinant SphK1 and SphK2 (FIG. 1B-E). This water-soluble sphingosine analog potently inhibited SphK1 activity in a dose-dependent manner (FIG. 1C) with 60-70% inhibition at 5 μM. As previously reported (Edsall et al., *Biochemistry*, 1998, supra.; and Kohama et al., *J Biol Chem*, 1998, supra.), N,N-dimethylsphingosine (DMS) also inhibited SphK1 activity, albeit with less potency. Importantly, in contrast to DMS, which also inhibits SphK2 (Liu et al., *J Biol Chem*, 2000, supra.) and ceramide kinase (Sugiura et al., *J Biol Chem* 277:23294-23300, 2002), our compound did not inhibit recombinant SphK2 (FIG. 1C,E) or ceramide kinase (data not shown). Thus, because of its specific inhibitory effect on SphK1, this compound is hereafter referred to as SK1-I.

Figure 1F:
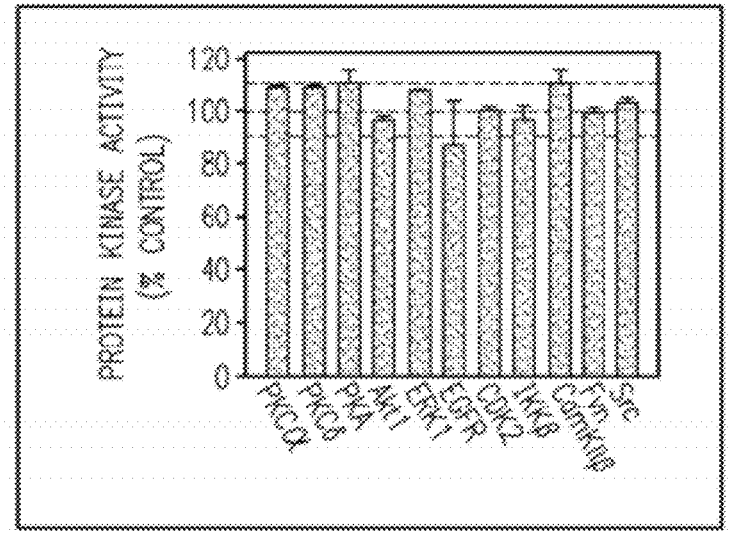

Lineweaver-Burk analysis revealed that SphKI activity was inhibited competitively by Sk1-I with a $K_i$ value of approximately 10 μM (FIG. 1D), nearly identical to the Km for sphingosine. SK1-I was not phosphorylated by either SphK1 or SphK2 (data not shown). Because DMS and several other pan SphK inhibitors also inhibit protein kinase C (Igarashi et al., Biochemistry 28:6796-6800, 1989) and potentially other kinases (De Luca et al., *Biofactors* 25:43-60, 2005; and Gamble et al., *Int J Cancer* 118:2412-2420, 2006), it was important to examine the effects of Sk1-I on protein kinases. A protein kinase activity screen was utilized which contained several different recombinant protein kinases, a fluorescently labeled polypeptide substrate and ATP at the $Km_{app}$ for each kinase. SK1-I did not significantly inhibit any of the protein kinases including two different members of the PKC family, PKCα and PKCδ, PKA, Akt1, ERKI, EGFR, CDK2, 1KKβ, or CamKIIβ (FIG. 1F). Hence, SK1-I is unique among known SphK inhibitors in view of its isozyme selectivity, water solubility, and lack of effect on protein kinases.

SK1-I Potently Inhibits Growth of Human Leukemia Cells

Figure 2A:
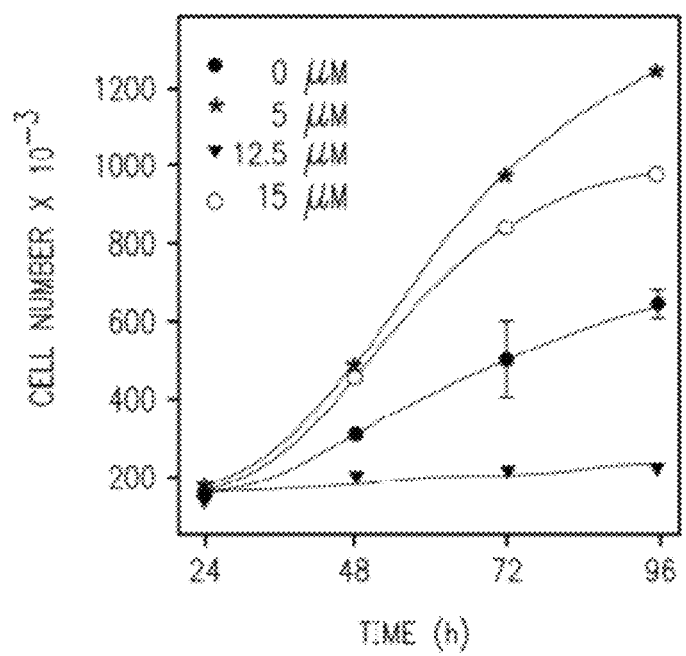
FIG. 2A shows concentration effects of SK1-I on the growth of U937 cells.
Figure 2B:
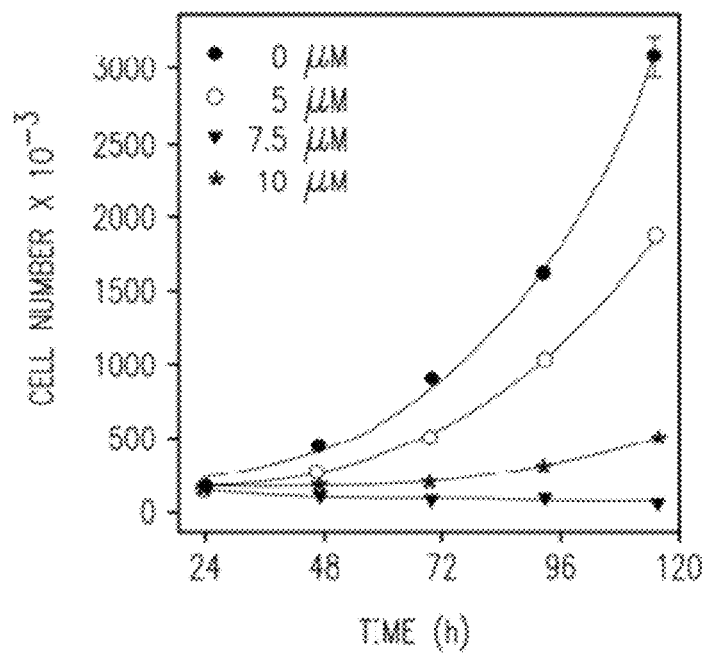
FIG. 2B shows concentration effects of SK1-I on the growth of T-lymphoblastic Jurkat cells.

Previous studies have shown that the pan SphK inhibitor DMS markedly induces apoptosis of U937 and Jurkat T cells (Cuvillier et al., *Nature*, 1996, supra.; Jarvis et al., *Mol Pharmacol* 52:935-947, 1997; Edsall et al., supra.; Hamada et al., *Biochem Biophys Res Commun* 244:745-750, 1998; and Cuvillier et al., *Blood*, 2001, supra.). As shown in FIG. 2A, a concentration of SK1-I as low as 5 μM significantly decreased growth of U937 cells cultured in the presence of 10% serum which was evident after 72 h of culture. T-lymphoblastic Jurkat cells were even more sensitive to SK1-I, as a concentration of 5 μM inhibited growth by 50% and 10 μM completely prevented cell growth (FIG. 2B). Similarly, 10 μM SK1-I decreased growth of other leukemia cell lines, including promyelocytic HL-60, Molt-4 T-cell leukemia, and K-562 CML cells by 50%, 70%, 90%, respectively, within 48 h of treatment.

Figure 2C:
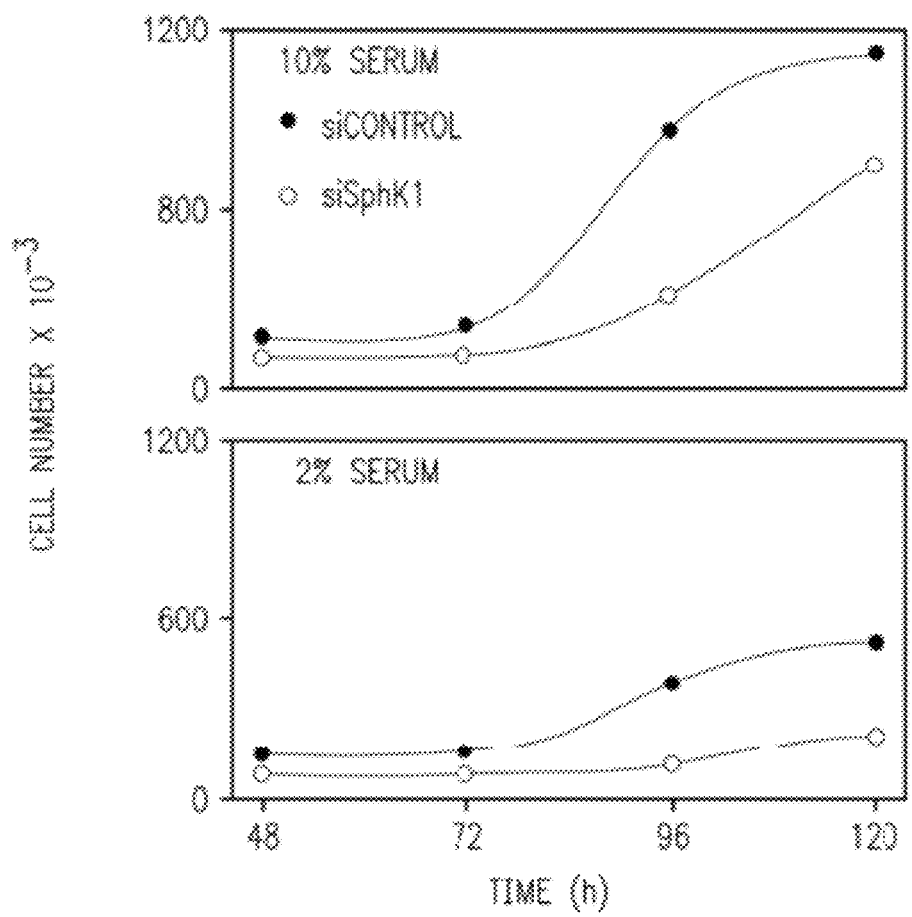
FIG. 2C shows the reduction in rate of growth of U937 cells with downregulation of SphK1 expression with siRNA targeting.
Figure 2C:
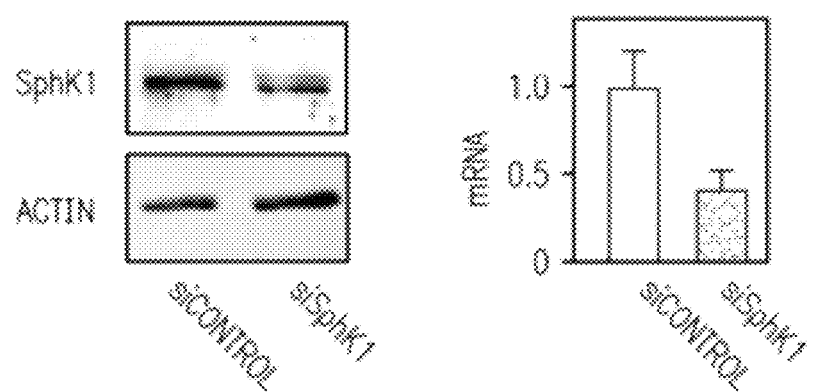

Similar to the effects of treatment with SK1-I and in agreement with studies in other leukemic cell lines (Bonhoure et al., supra.; and Baran et al., supra.) downregulation of SphK1 expression with siRNA targeted to a unique sequence, which reduced SphK1 protein and mRNA levels by more than 60% (FIG. 2C), markedly reduced the rate of growth of U937 cells cultured in the presence of either 2% or 10% serum (FIG. 2C). Together, these findings are consistent with the notion that specific inhibition of SphK1 by pharmacologic or genetic means significantly inhibits the growth of human myeloid and lymphoid leukemia cells.

SKI-I Induces Apoptosis in Human Leukemia Cells

Figure 2D:
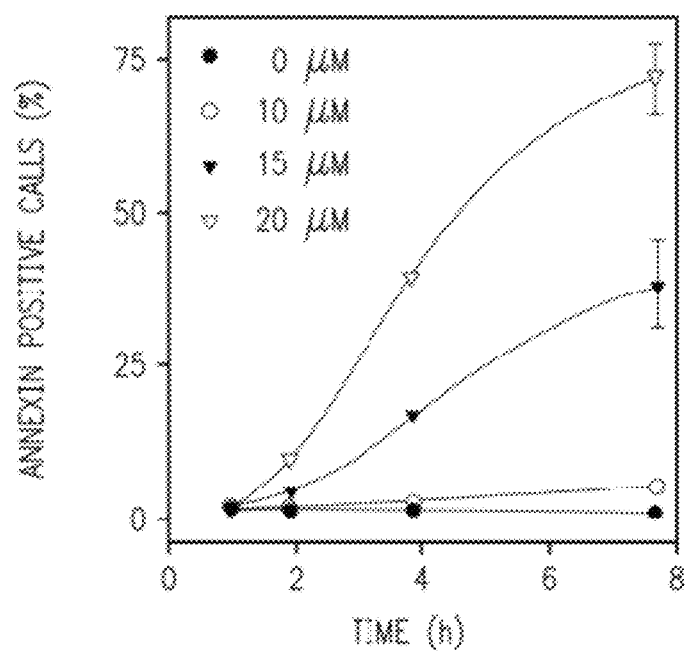
FIG. 2D shows time- and concentration-dependent increases in apoptosis of U937 cells upon exposure to SK1-I.
Figure 2F:
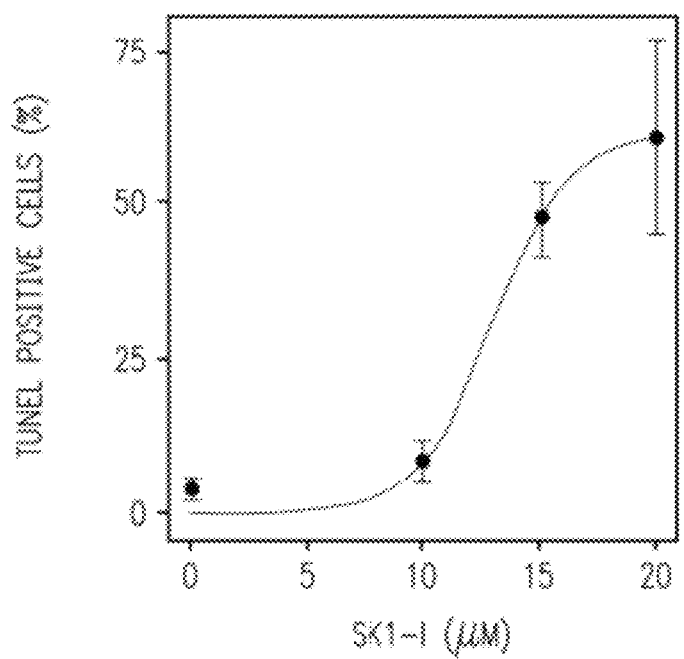
FIG. 2F shows the results correlating closely with DNA strand breakage as determined by TUNEL assays.
Figure 2E:
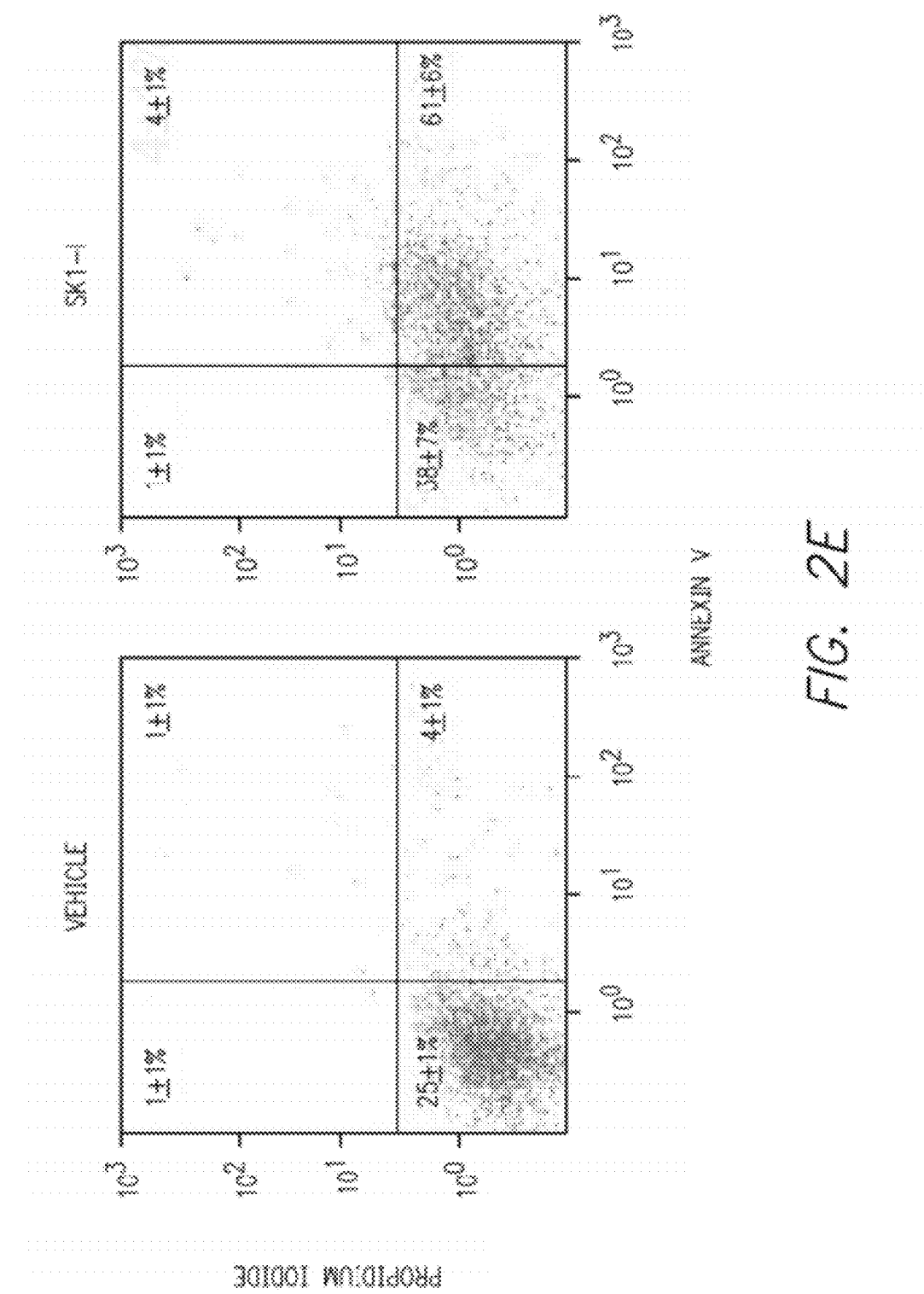
FIG. 2E illustrates the status of the U937 cells in that majority were early apoptotic and small percentage were necrotic (PI-positive).
Figure 2G:
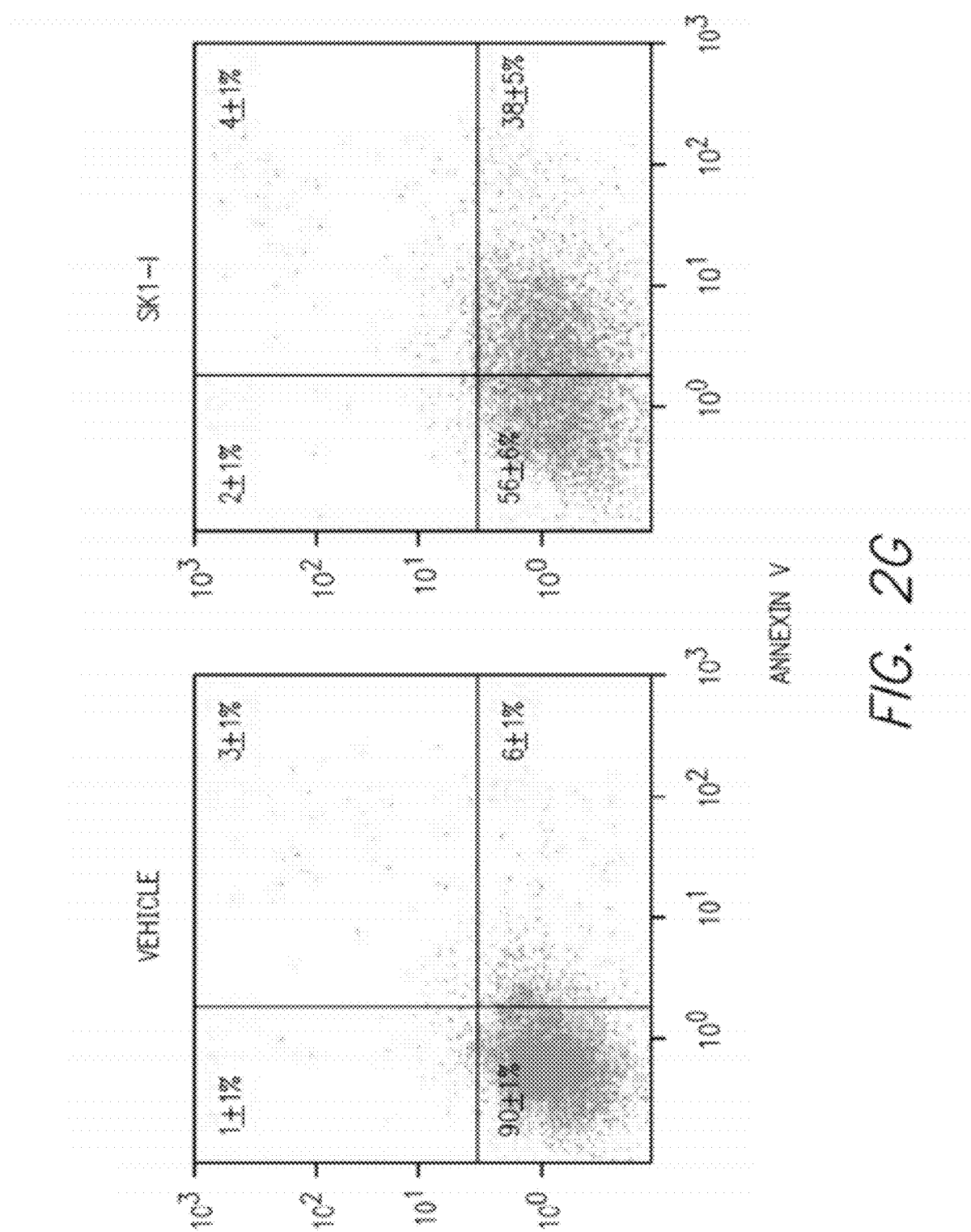
FIG. 2G shows the serum concentration effects on U937 cells.

Inhibition of SphK with DMS or downregulation of SphK1 expression has been associated with induction of apoptosis in many cell types, including human leukemia cells (Cuvillier et al., Nature, 1996, supra.; Jarvis et al., 1998, supra., Jendiroba et al., 2002, supra.; and Bonhoure et al., supra.). Thus, we next examined the effects of Sk1-I on apoptosis of U937 cells using flow cytometry to monitor cells expressing phosphatidylserine on the outer plasma membrane by annexin V staining and PI as a measure of membrane permeability. There was a time- and concentration-dependent increase in apoptosis of U937 cells upon exposure to SK1-I (FIG. 2D). As shown in FIG. 2E, the majority of the cells were early apoptotic and a very small percentage were necrotic (PI-positive only). These results correlated closely with the occurrence of DNA strand breaks, as determined by TUNEL assays (FIG. 2F). Moreover, similar to downregulation of SphKI, which inhibits cell growth more effectively when cells are cultured in the presence of lower concentrations of serum (FIG. 2C), U937 cells were more susceptible to SK1-I-induced apoptosis when the serum concentration was reduced (FIG. 2G).

Figure 3A:
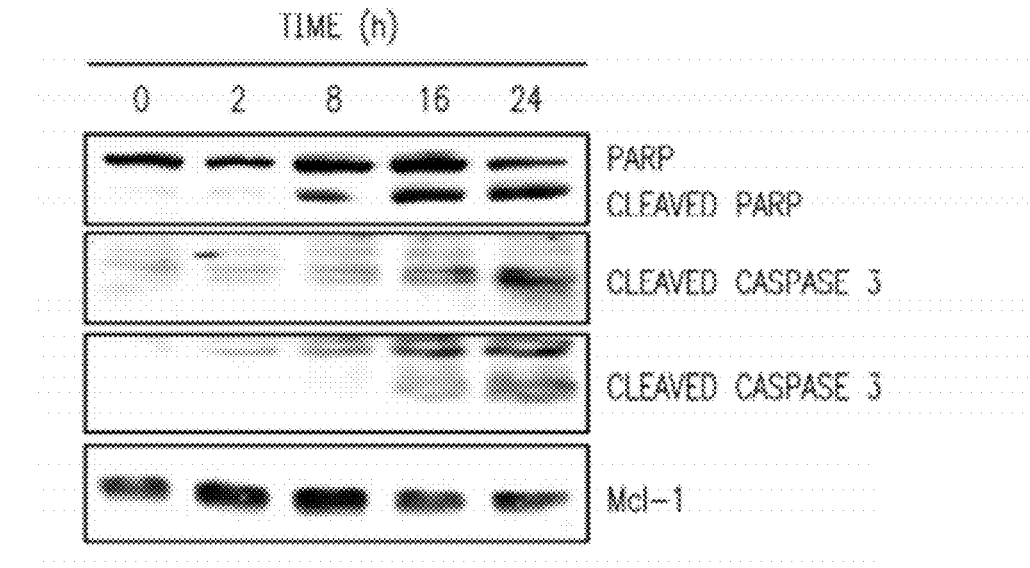
FIGS. 3A and 3B show treatment of U937 cells with SK1-I increased activation of caspase-3 and caspase-9 and induced cleavage of poly ADP ribose polymerase (PARP) with induction of apoptosis.
Figure 3B:
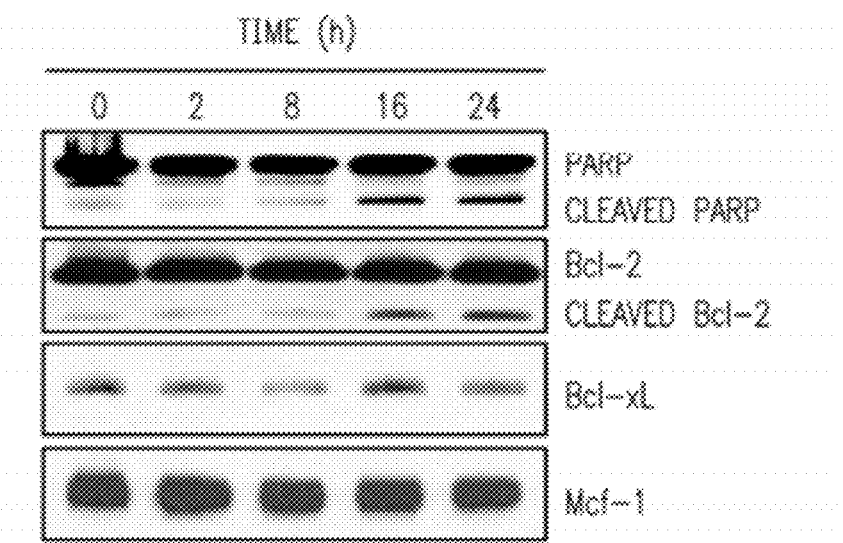
Figure 3C:
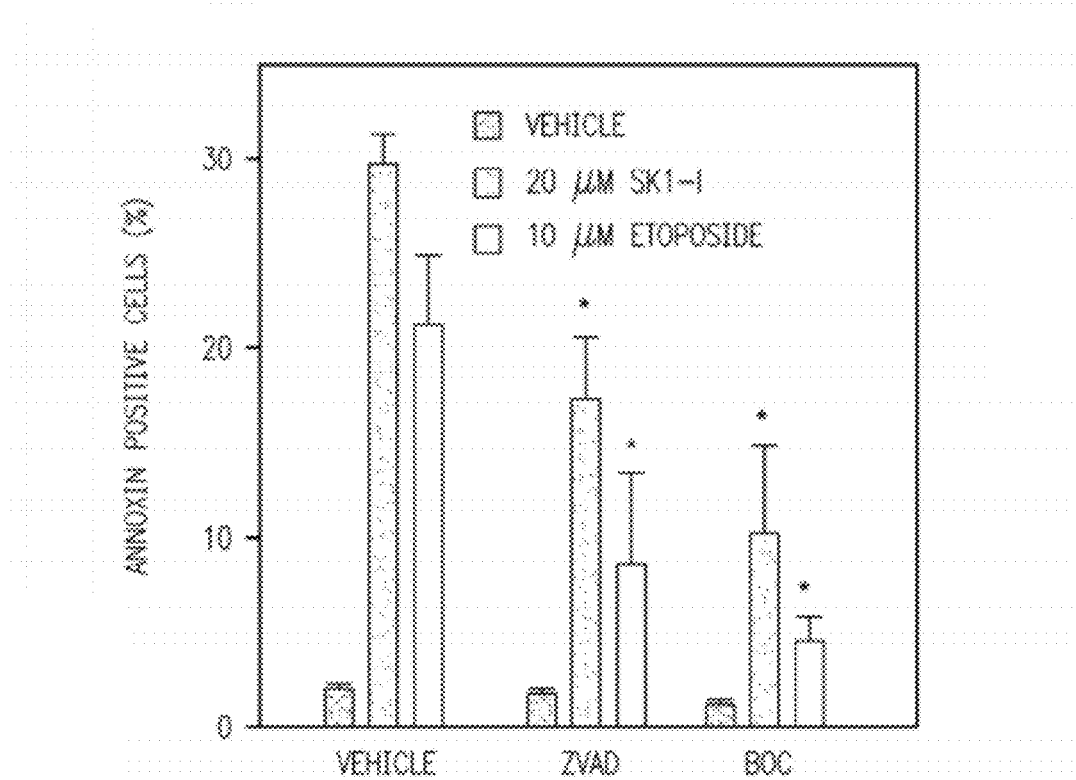
FIG. 3C shows the results of pretreatment of U937 cells with pan-caspase inhibitors ZVAD and BOC on SK1-I-induced apoptosis and inducement by DNA damaging agent etoposide.
Figure 3D:
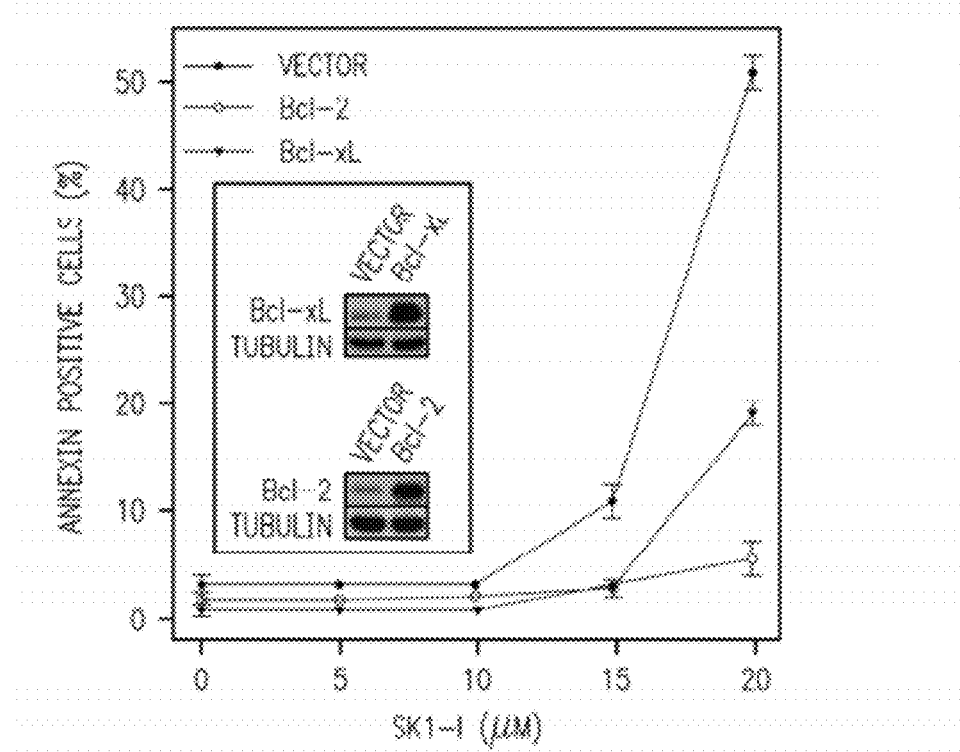
FIG. 3D shows the effect of ectopic expression of Bcl-2 against SK1-I-induced lethality.

Functional Roles of Caspase Activation and Bcl-2 Cleavage in SK1-I-Induced Cell Death It has previously been demonstrated that downregulation of SphK1 in HL-60 cells with siRNA (Bonhoure et al., supra.) or inhibition of SphK with DMS in Jurkat cells (Cuvillier et al., *J Biol Chem* 275:15691-15700, 2000) is sufficient to trigger activation of executioner caspase-3 as well as cleavage of PARP, hallmarks of apoptosis. Similarly, concomitant with induction of apoptosis, treatment of U937 cells with SK1-I increased activation of caspase-3 and -9 and induced cleavage of poly ADP ribose polymerase (PARP) (FIG. 3A,B). Furthermore, exposure to Sk1-I for 16-24 h resulted in cleavage of Bcl-2 (FIG. 3B), an anti-apoptotic protein that prevents mitochondrial dysfunction. On the other hand, levels of Mcl-1, an anti-apoptotic protein that plays a key role in the survival of malignant hematopoietic cells (Moulding et al., *Blood* 96:1756-1763, 2000), were not significantly altered (FIG. 3A,B). Next, we investigated the functional roles of caspase activation and Bcl-2 cleavage in Sk1-I-induced lethality. Pretreatment of U937 cells with the pan-caspase inhibitors ZVAD and BOC significantly attenuated SK1-I-induced apoptosis as well as that induced by the DNA damaging agent etoposide (FIG. 3C). Furthermore, ectopic expression of Bcl-2 completely protected against Sk1-I-induced lethality and expression of Bcl-xL reduced cell death by 60% (FIG. 3D). Together, these findings indicate that the lethality of SK1-I is primarily mediated via the intrinsic mitochondrial pathway, an event opposed by Bcl-2.

Figure 4A:
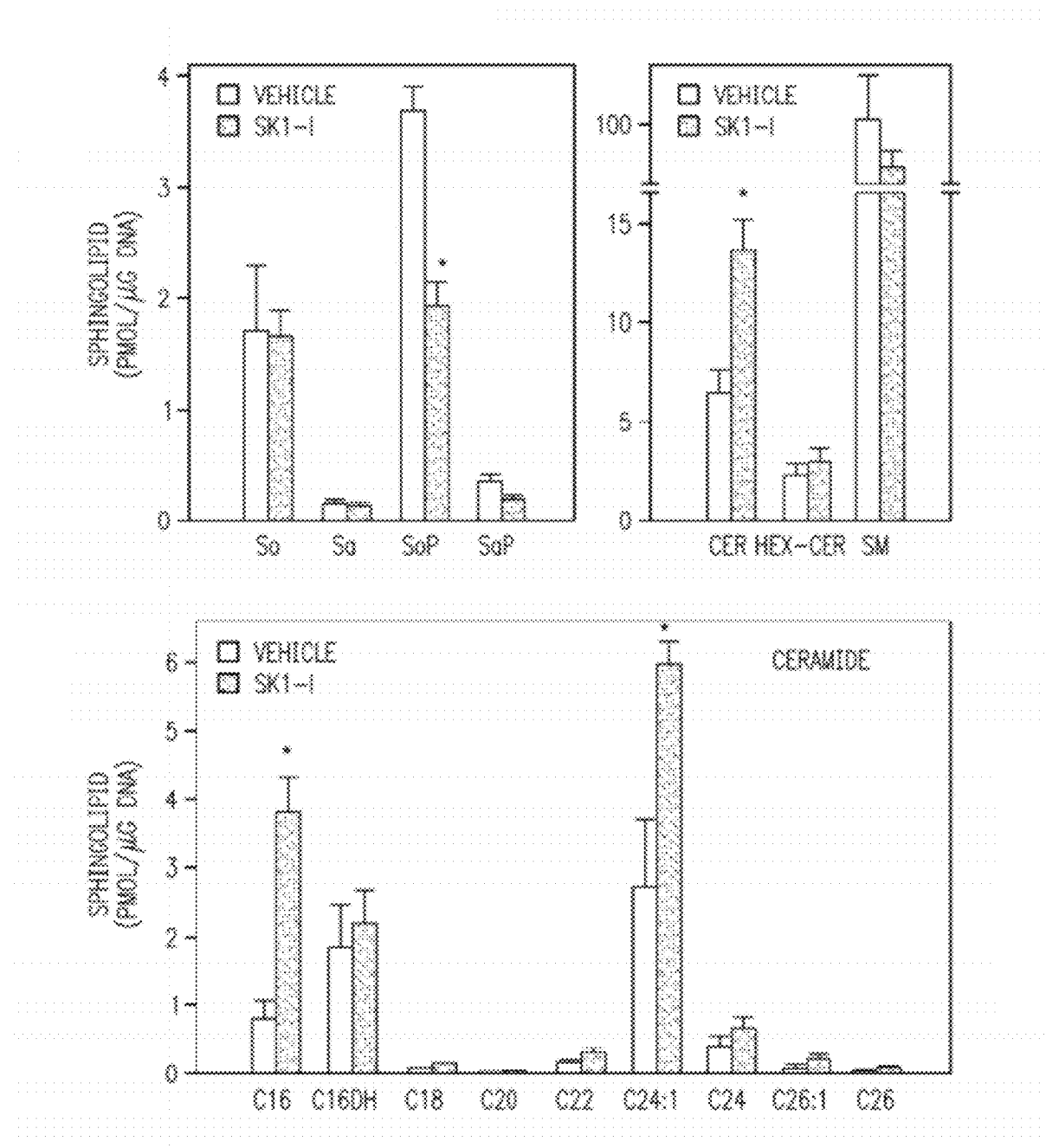
FIG. 4A shows the effects of SK1-I on levels of sphingolipid metabolites as determined by HPLC ESI-MS/MS.

Because SphK1 is a critical regulator of the balance between pro-apoptotic ceramide and anti-apoptotic S1P (Olivera et al., supra.; and Bonhoure et al., supra.), the effect of SK1-I on levels of these sphingolipid metabolites were determined by high performance liquid chromatography ESI-MS/MS (Sullards et al., supra.). Sk1-I treatment caused a 50% decrease in total cellular S1P (FIG. 4A), without altering levels of sphingosine or dihydrosphingosine (sphinganine), with a concomitant increase in total cellular ceramide and a decrease in sphingomyelin (FIG. 4A). The most abundant ceramide species in U937 cells was 24:1 (FIG. 4A). Sk1-I treatment increased levels of C16:0 and C24:1 ceramide species by 3- and 2-fold, respectively, but had no significant effects on other ceramide species (FIG. 4A).

Figure 4B:
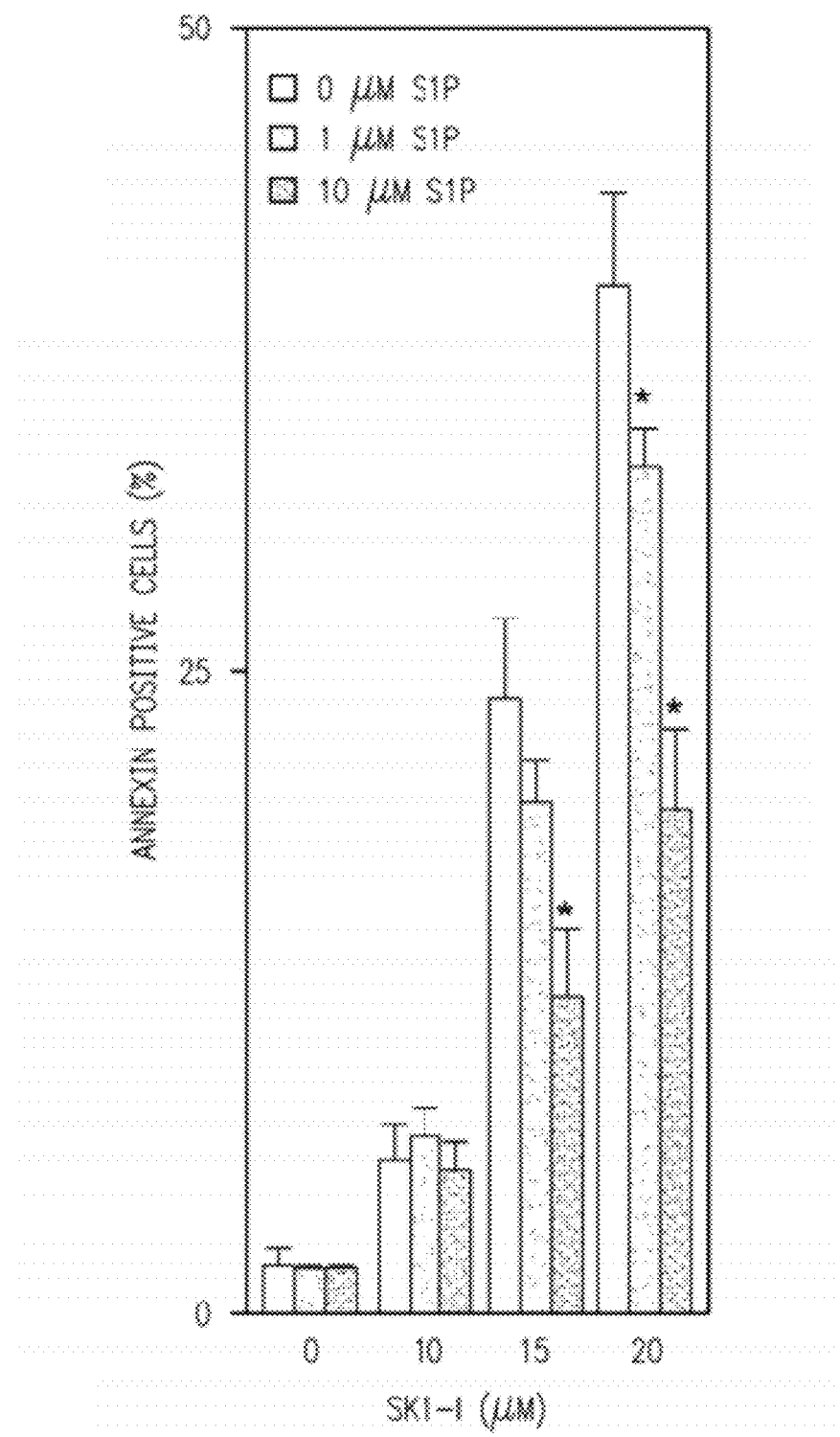
FIG. 4B shows the results of SK1-I-induced apoptosis by adding exogenous S1P in a dose-dependent manner.

To confirm that the apoptotic effects of SK1-I were due to its ability to inhibit SphK1, S1P add-back experiments were carried out. Consistent with the reduction in levels of S1P by SK1-I, apoptosis induced by SK1-I was diminished by addition of exogenous S1P in a dose-dependent manner (FIG. 4B). Collectively, these findings indicate that SK1-I induces apoptosis in human leukemia cells by inhibiting SphK1 and production of S1P with a concomitant increase in ceramide.

Figure 5A:
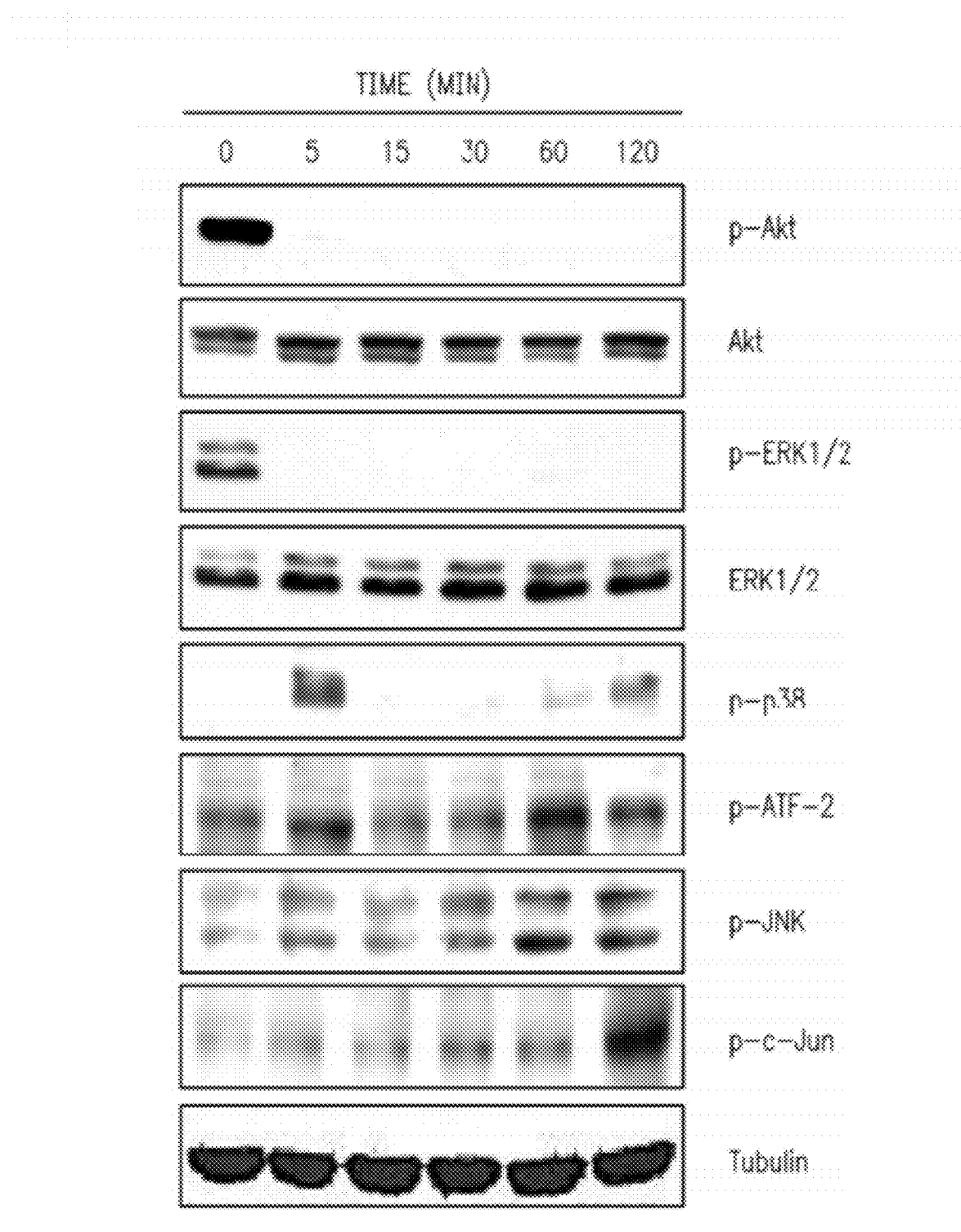
FIGS. 5A-C show the decrease in phosphorylation of ERK1/2 and Akt when U937 cells were treated with SK1-I.
Figure 5B:
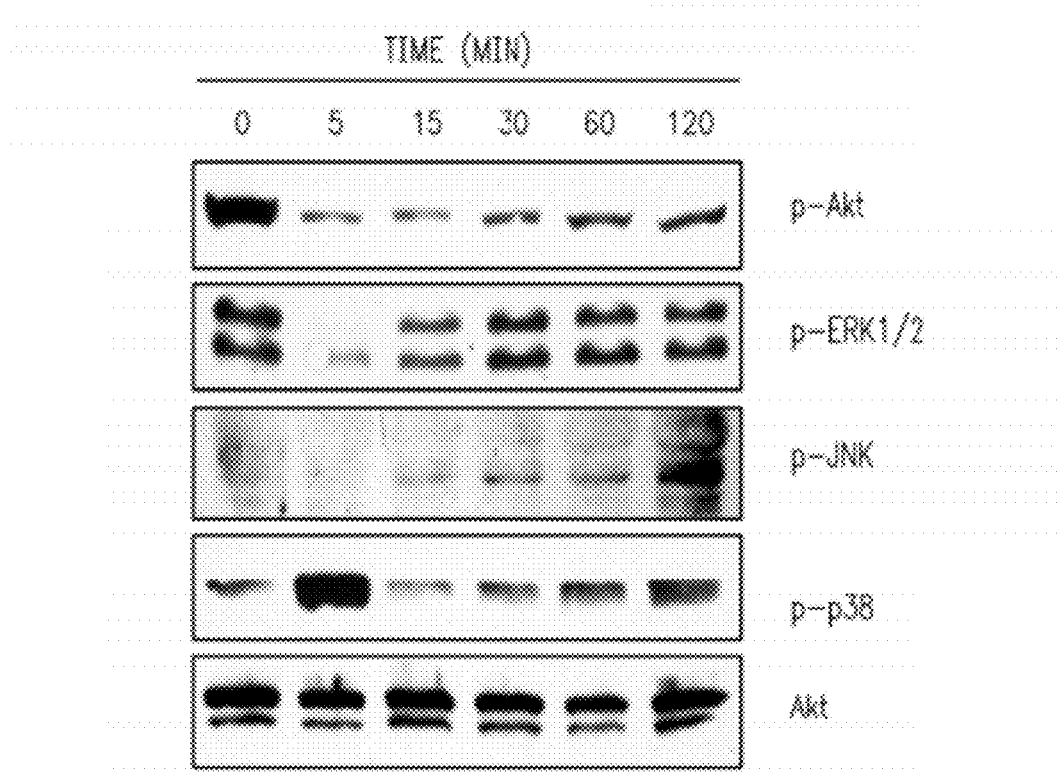
Figure 5C:
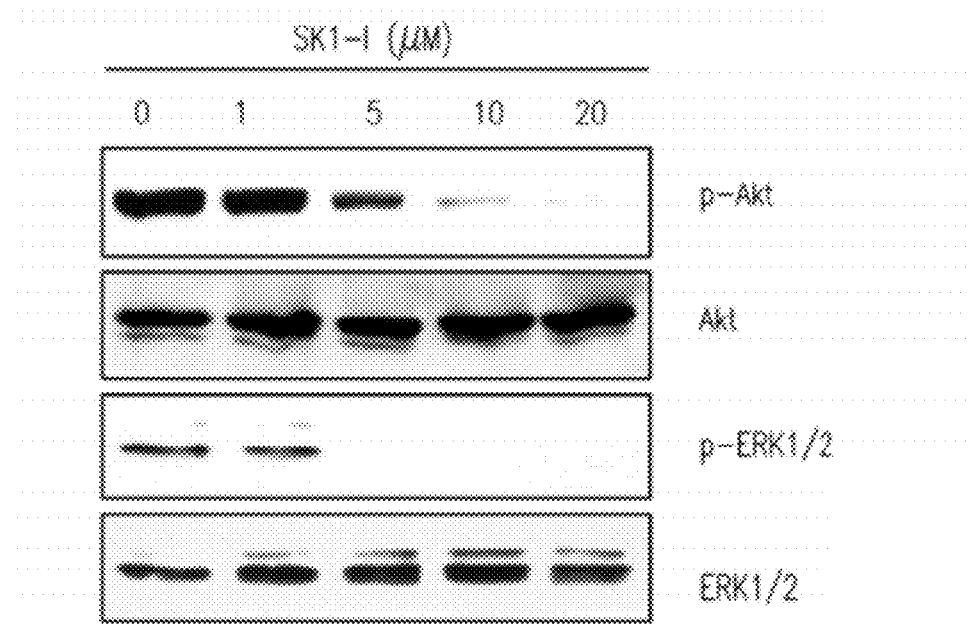
Figure 5D:
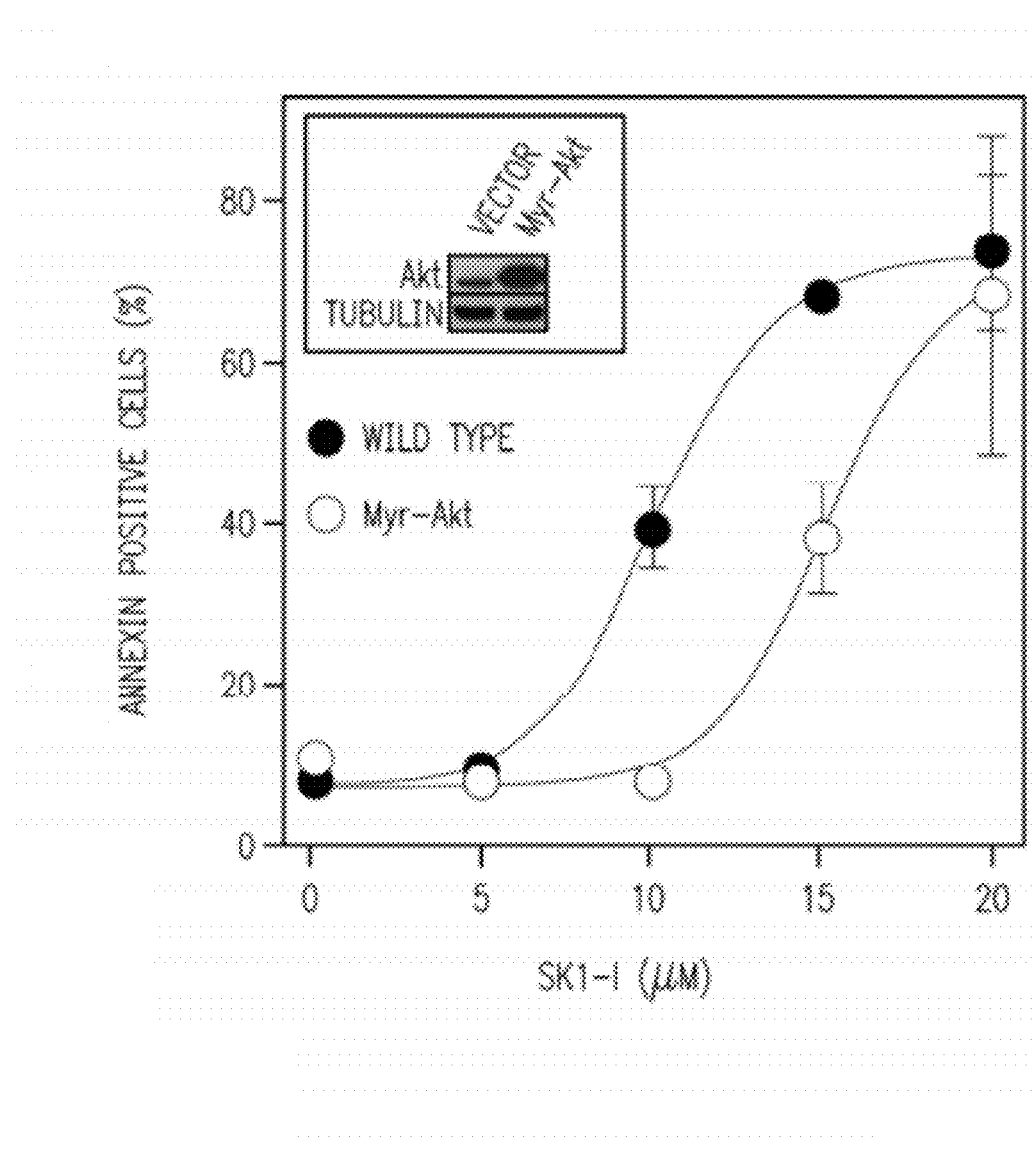
FIG. 5D shows the effect of overexpression of constitutively active myristoylated Akt in U937 cells on SK1-I-induced apoptosis at concentrations below 15 μM.

Apoptosis Induced by SKI-i is Associated With Inactivation of ERK1/2 and Akt Survival Signals Abundant evidence indicates that the mitogen-activated protein kinases (ERK1/2, JNK, and p38 MAPK) and Akt play a critical role in leukemia cell fate (Steelman et al., *Leukemia* 18:189-218, 2004). Treatment of U937 cells with SK1-I caused a rapid and marked decrease in phosphorylation of ERK1/2 and Akt (FIG. 5A-C). These deactivations of survival signaling were sustained up to 2 h in the presence of low concentrations of serum (FIG. 5A), whereas in the presence of 10% serum, the attenuation of p-ERK1/2 and p-Akt levels was gradually overcome (FIG. 5B) and was dependent on the concentration of Sk1-I (FIG. 5C). Furthermore, a transient increase in p38 phosphorylation was observed at 5 min followed by a later less robust activation (FIG. 5A,B). Additionally, JNK activation and c-Jun phosphorylation were also detected at later times (FIG. 5A,B). Because SK1-I profoundly deactivates Akt, it was of interest to determine its role in the lethal effects of SK1-I. Overexpression of constitutively active myristoylated Akt in U937 cells significantly attenuated apoptosis induced by SK1-I at a concentration below 15 μM (FIG. 5D), suggesting that deactivation of Akt might be one of the factors contributing to the apoptotic effects of Sk1-I.

Primary Human AML Blasts are Highly Sensitive to Apoptosis Induced By SK1-I

Figure 6A:
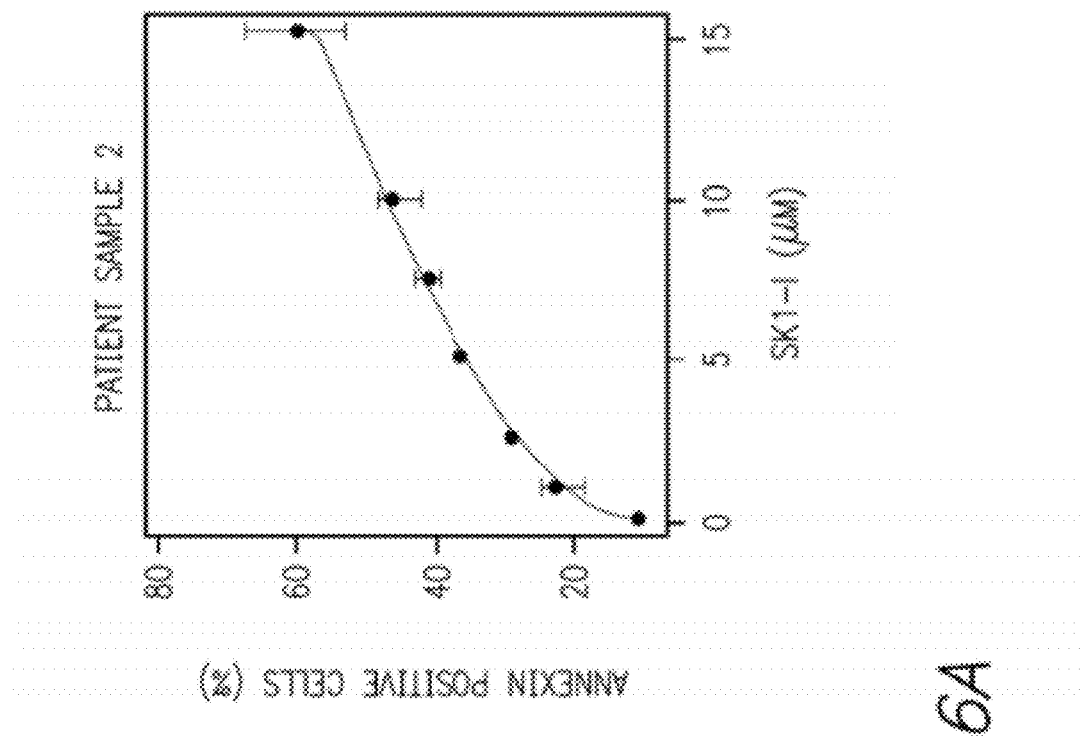
FIGS. 6A and 6B show increases in apoptosis in two patient samples when exposed to SK1-I.
Figure 6A:
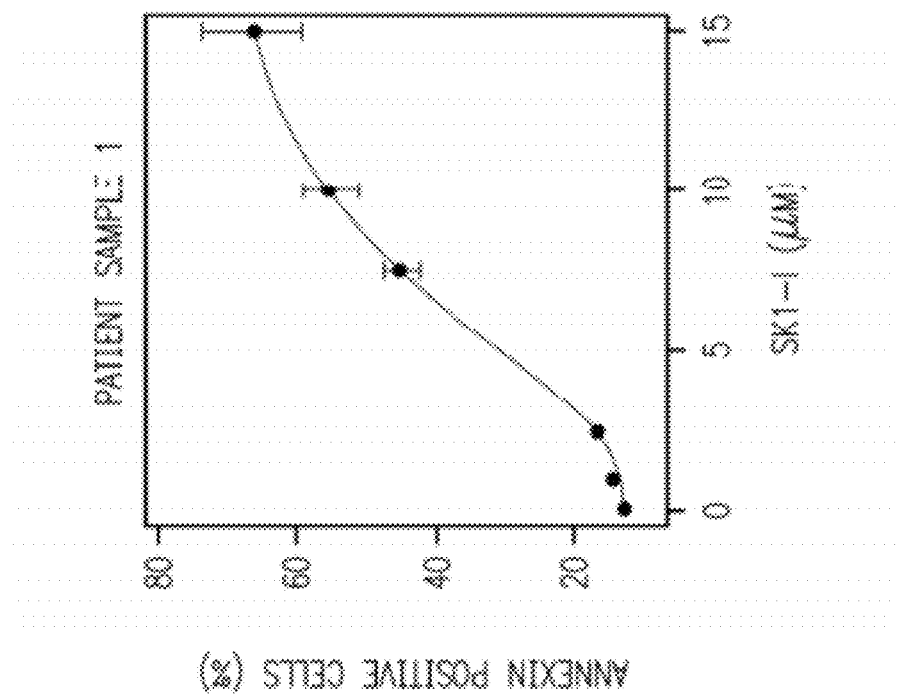
Figure 6B:
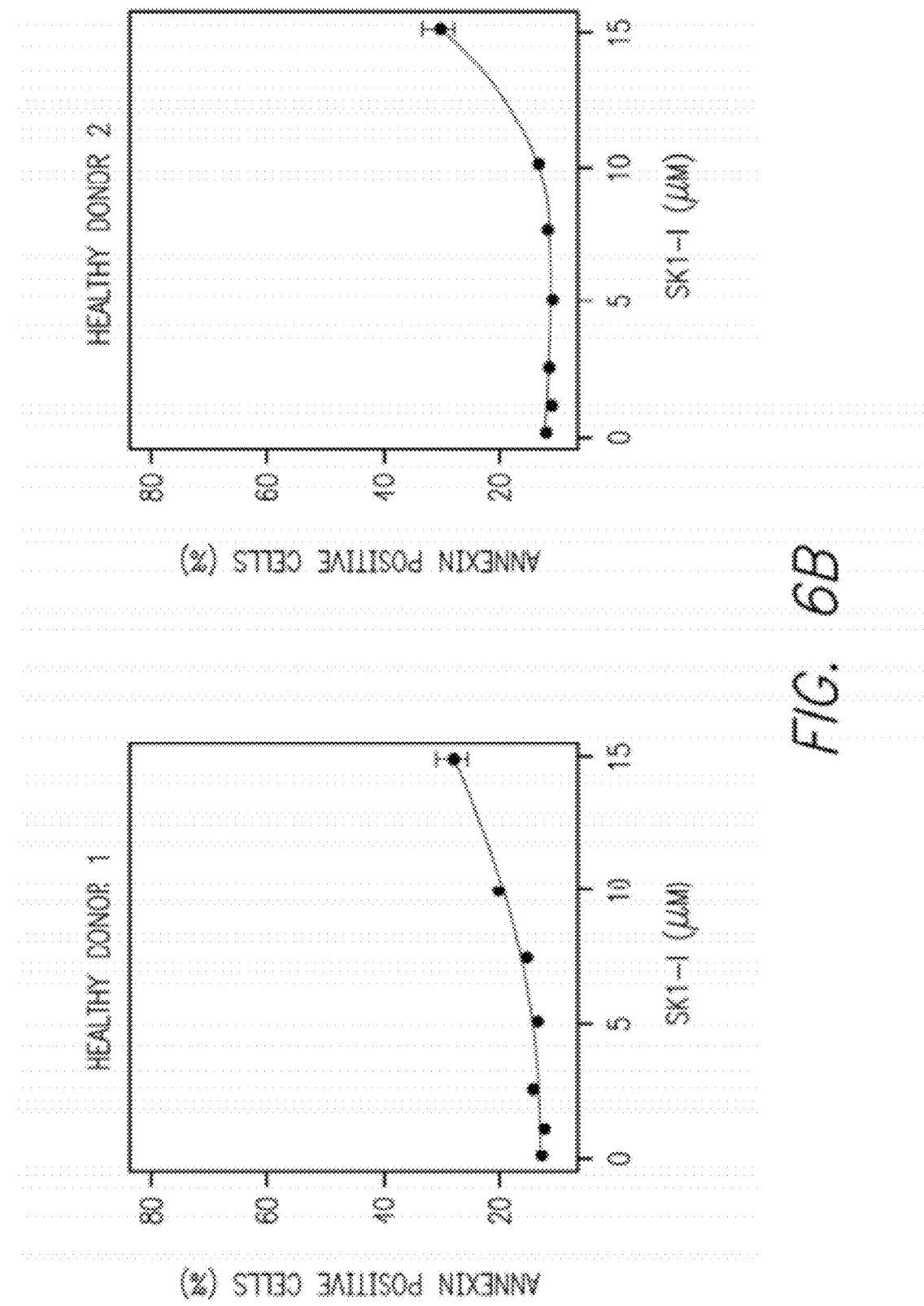

To examine the effectiveness of SK1-I on primary AML specimens, parallel studies were performed in leukemic blasts obtained from bone marrow aspirates of two patients with AML (FAB subtype M2). Treatment of blasts with increasing concentrations of Sk1-I revealed enhanced sensitivity to apoptosis induction compared to U937 and Jurkat cell lines. Both patient samples exhibited a marked increase in apoptosis when exposed to Sk1-I for 24 h and 40-50% apoptosis was observed with 7.5 μM Sk1-I as revealed by annexin V/PI analysis (FIG. 6A). In agreement with previous results (Rosato et al., *Mol Cancer Ther* 6:692-702, 2007), less than 10% of blasts exhibited apoptosis in the absence of treatment which is very similar to apoptosis of normal peripheral blood mononuclear cells. Notably, SK1-I had a much less pronounced effect on the survival of normal peripheral blood mononuclear cells (FIG. 6B). These results suggest that primary human AML cells, reported to overexpress Sphk1 (Sobue et al., *Leukemia* 20:2042-2046, 2006), are more susceptible to Sk1-I than continuously cultured leukemia cell lines, while SK1-I is relatively sparing to normal peripheral blood mononuclear leukocytes.

Antileukemic Activity of SKI-I In Vivo.

Figure 7A:
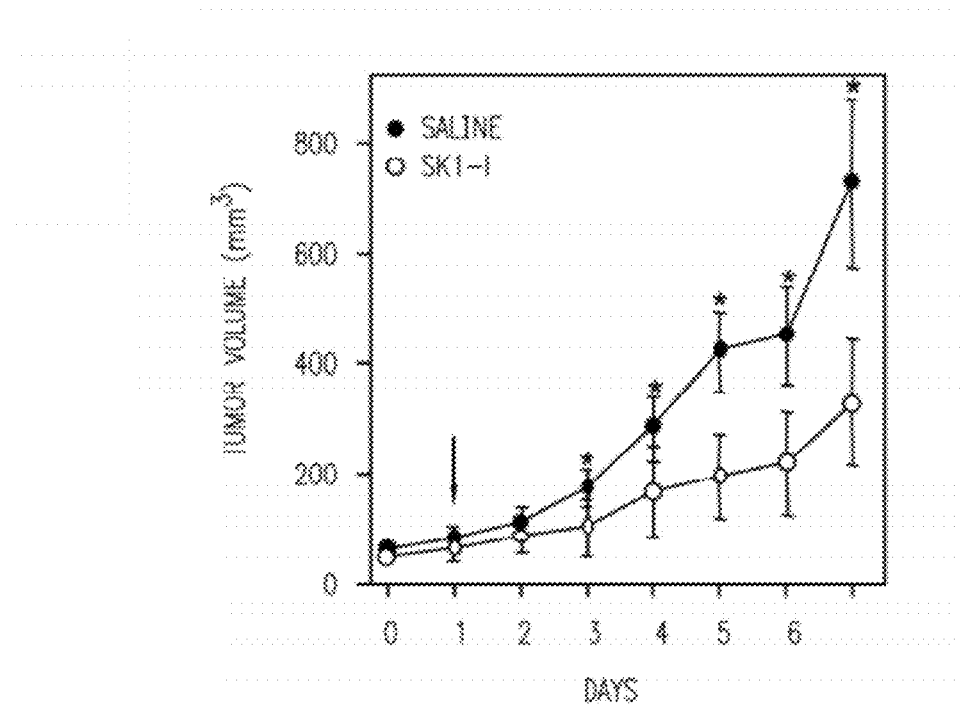
FIG. 7A show the decrease in tumor growth in xenografts in immunodeficient mice with SK1-I administration.
Figure 7B:
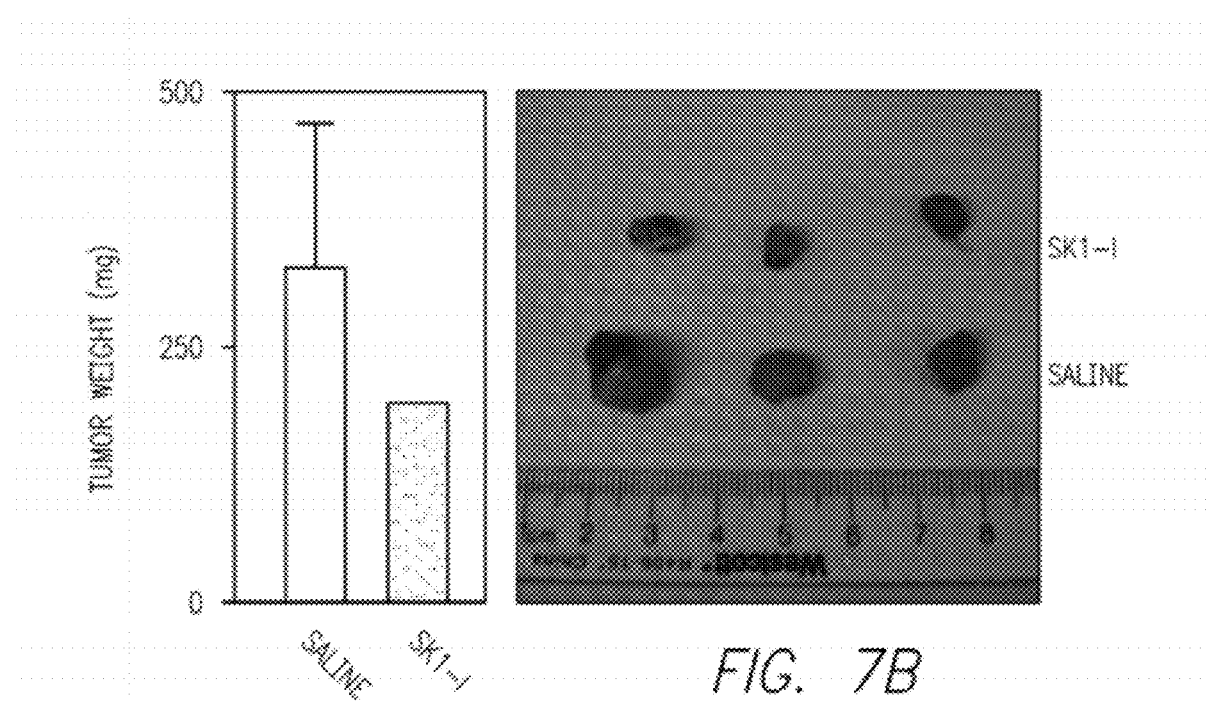
FIG. 7B shows the effects of SK1-I treatment on tumor weights in mice.

We next evaluated the ability of SKi-I to inhibit tumor growth of leukemia cells in xenografts in immunodeficient mice, a model that has been extensively used to facilitate development of several new treatment modalities (McCormack et al., *Leukemia* 19:687-706, 2005). U937 cells subcutaneously injected into the flanks of SCID/beige mice rapidly gave rise to exponentially growing tumors. When tumors reached a volume of 50-100 mm$^3$, mice were injected intraperitoneally with saline or Sk1-I (20 mg/kg) daily. As can be seen in FIG. 7A, SK1-I significantly decreased tumor growth. After 7 d, the mean volume of the U937 tumors in mice treated with SK1-I was more than 50% smaller than the tumors in the saline treated mice (control group mean=747 mm$^3$, Sk1-I group mean=332 mm$^3$, p<0.001). Tumor weights at autopsy of Sk1-I-treated mice were also significantly lower (FIG. 7B). Mice treated with Sk1-I did not show signs of wasting and the body weights after 7 d were not significantly different than controls.

Figure 7C:
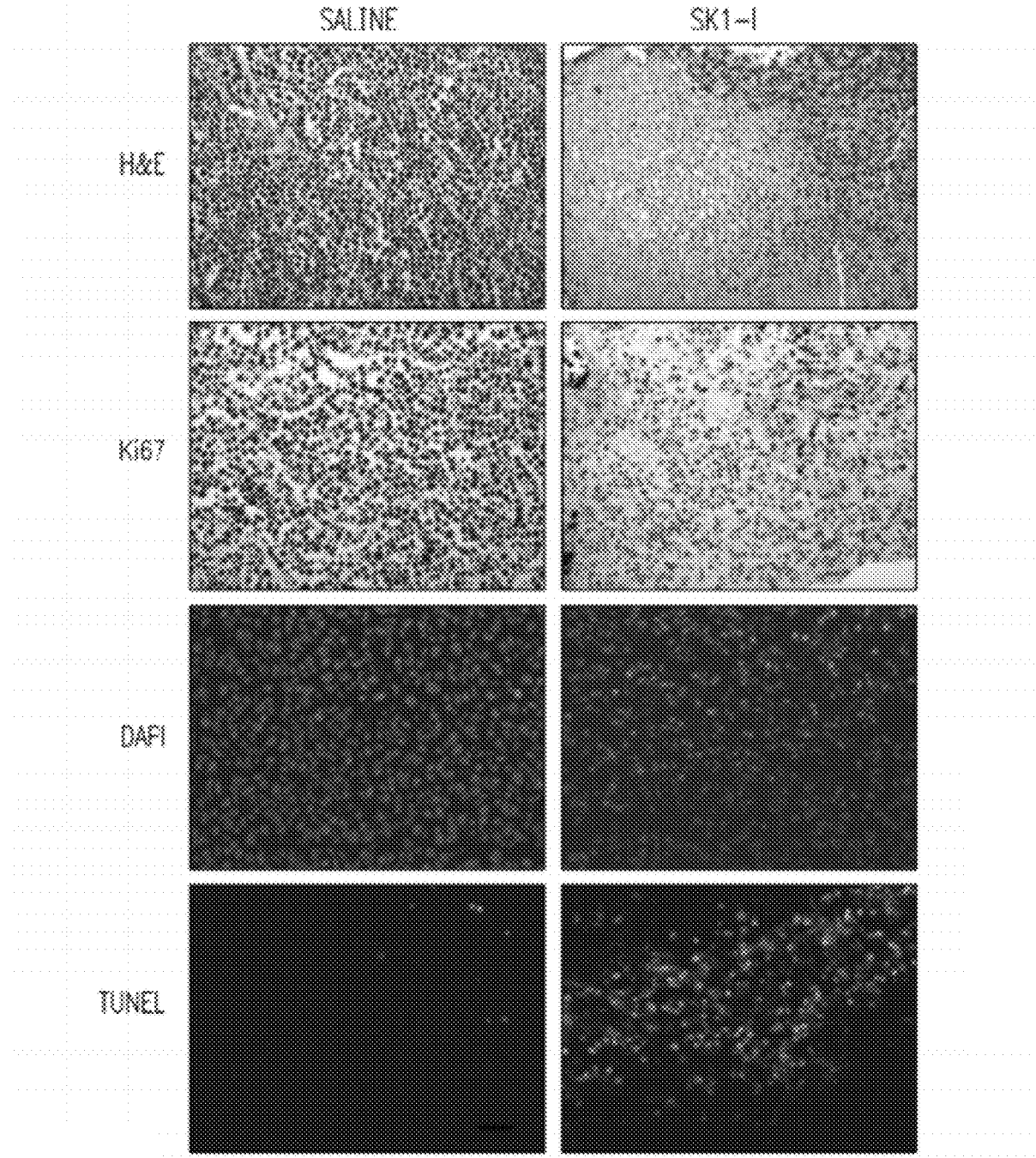
FIG. 7C shows immunohistochemical analysis of tumors from SK1-I treated mice.

As expected, tumors from saline treated mice stained strongly with Ki67 indicating a tumor composition of highly proliferating cells with very few apoptotic cells stained by TUNEL (FIG. 7C). In contrast, immunohistochemical analysis of tumors from Sk1-I treated mice revealed many apoptotic cells as determined by nuclear fragmentation (TUNEL staining) and condensed nuclei (FIG. 7C). SK1-I also drastically reduced mitotic cells in the tumors (FIG. 7C). These results indicate that Sk1-I has potent anti-leukemic activity in vivo.

Discussion

Ample evidence indicates that in many types of cancers, S1P production is dysregulated leading to abnormal cell growth and survival signaling (Milstien et al., supra; and R A Sabbadini, *Br J Cancer* 95:1131-1135, 2006). Sphk1 is overexpressed in a variety of solid tumors (French et al., *Cancer Res* 63:5962-5969, 2003) and also in AML (Sobue et al., supra.). Moreover, bcr/abl, a common genetic aberration in chronic myelogenous leukemia and a poor prognostic indicator for at least 20% of patients with acute lymphocytic leukemia, has been shown to upregulate SphK1 expression (Li et al., *Oncogene* 26:7904-7908, 2007). Hence, SphK1 is now considered to be a potential target for pharmacologic intervention, particularly in leukemic cells where its level correlates with chemoresistance and radioresistance (Bonhoure et al., supra.; and Baran et al., supra.). Previous studies of the role of SphKi in leukemic cells have focused on its downregulation by specific siRNA or the use of pharmacological agents that inhibited both SphK1 and Sphk2, and potentially protein kinases. This study describes the development of the first potent and water soluble SphK1 isozyme specific inhibitor, Sk1-I. Moreover, Sk1-I does not inhibit PKC or a large number of other protein kinases. In contrast to most small molecule protein kinase inhibitors that are competitive with ATP at the well-conserved ATP-binding pocket and potentially cross-react, Sk1-I is competitive with the lipid substrate.

Sk1-I potently induced apoptosis in several leukemic cells lines and AML leukemic blasts, reflected by externalization of phosphatidylserine, increased DNA strand breaks, activation of caspases 3 and 9, and cleavage of PARP and Bcl-2. By what mechanisms does Sk1-I so profoundly induce these lethal effects? This could be due to several non-mutually exclusive interrelated actions. Sk1-I inhibits production of pro-survival S1P that can act intracellularly to enhance growth and survival, although its intracellular targets have not yet been elucidated (Kohno et al., *Mol Cell Biol* 26:7211-7223, 2006). It is also well accepted that intracellularly produced S1P can be released from cells (Mitra et al., *Proc Nat Acad Sci USA* 103:16394-16399, 2006) and act through its cell surface receptors that are linked to survival pathways including ERKI/2 and Akt (Spiegel et al., supra.). In this regard, the ability of SK1-I to decrease activated ERK1/2 and Akt in leukemic cells might be relevant, as the Raf/MEK/ERK and PI3K/Akt pathways are frequently constitutively activated in AML (Steelman et al., supra.; and Nyakern et al., *Leukemia* 20:230-238, 2006). Because ERK1/2 phosphorylates and activates SphK1 (Pitson et al., *J Exp Med* 201:49-54, 2005), leading to increased S1p which in turn can stimulate ERK1/2, Sk1-I can interrupt this positive feedback loop by inhibiting SphK1, decreasing pro-growth and survival S1P while simultaneously increasing its precursor, the pro-apoptotic ceramide. Hence, Sk1-I integrates multiple molecular therapeutic targets in leukemia.

Ceramide generation has long been implicated in apoptosis induction in human leukemia cells (Jarvis et al., *Proc Natl Acad Sci USA* 91:73-77, 1994), and recently, the synergistic actions of several different signal transduction inhibitors on apoptosis have been linked to dramatic increases in ceramide generation. For example, co-administration of histone deaceylase inhibitors with perifosine in human leukemia cells leads to Akt and ERK disruption, a marked increase in ceramide and reactive oxygen species production, and a striking increase in mitochondrial injury and apoptosis (Rahmani et al., supra.; and Rosato et al., *Mol Pharmacol* 69:216-225, 2006). Ceramide can transduce its apoptotic actions via multiple pathways (Ogretmen et al., supra.). Important identified ceramide targets include the serine/threonine protein phosphatases PP1 and PP2A that dephosphorylate Akt as well as SR proteins, regulators of alternative splicing of Bcl-2 (Ogretmen et al., supra.). We found that exposure to Sk1-I resulted in cleavage of Bcl-2, a response that has been associated with mitochondria-dependent apoptosis (Cheng et al., *Science* 278:1966-1968, 1997). Moreover, it is well established that overexpression of Bcl-2 prevents ceramide formation and protects against ceramide-induced apoptosis in many cell types including acute lymphoblastic leukemia and AML (Zhang et al., *Proc Natl Acad Sci USA* 93:5325-5328, 1996; Amarante-Mendes et al., *Blood* 91:1700-1705, 1998; and Ogretmen et al., supra.) (In agreement, we found that overexpression of Bcl-2 also prevented Sk1-I-induced lethality, emphasizing the importance of the intrinsic mitochondrial death pathway. Consistent with this notion, it has recently been demonstrated that S1P exerts its cytoprotective effect on mitochondrial events during apoptosis of Jurkat cells by blocking translocation of Bax to the mitochondria in a MEK/ERK1/2-dependent manner (Betito et al., *biochem Biophys Res Commun* 340:1273-1277, 2006). A recent study suggested that sustained elevation of ceramide at the endoplasmic reticulum coordinately activates the ER stress response and inactivates anti-apoptotic Akt leading to apoptosis (Swanton et al., *Cancer Cell* 11:498-512, 2007). It is thus possible that SK1-I-induced Akt deactivation is mediated not only by decreased formation of S1P, but also by increased ceramide. The immunosuppressant drug FTY720, which structurally resembles SK1-1, but is a competitive substrate of SphKs rather than a competitive inhibitor, has also been shown to reduce Akt phosphorylation (Ng et al., *Int J Oncol* 30:375-380, 2007). FTY72O, which had relatively little toxicity in clinical trials for multiple sclerosis (Brinkman et al., *Pharmacol Ther* 115:84-105, 2007) has recently been proposed to be an alternative for treating blast crisis chronic myelogenous leukemia and Philadelphia chromosome-positive acute lymphocytic leukemia (Neviani et al., *J Clin Invest* 117:2408-2421, 2007).

Our finding that Sk1-I potently induced apoptosis in leukemic blasts isolated from patients with AML but was relatively noncytotoxic to normal peripheral blood mononuclear leukocytes highlights its selectivity for leukemia cells. Moreover, in a xenograft AML model, SK1-I had clear single agent activity that suppressed tumor growth, induced apoptosis in the tumor, and decreased proliferation, analogous to its actions in vitro. Preliminary analysis of toxicity of liver, kidney, and spleen did not reveal any noticeable effects. Thus, specific SphK1 inhibitors deserve consideration for potential pharmacologic intervention in leukemia, used either alone or as adjuncts to conventional or other known targeted agents.

Many obvious variations will no doubt be suggested to those of ordinary skill in the art, in light of the above detailed description and examples of the present invention. It will be appreciated by those skilled in the art that any arrangement which is calculated to achieve the same purpose may be substituted for the specific embodiments shown. This application and invention are intended to cover any adaptations or variations of the present invention. All such variations are fully embraced by the scope and spirit of the invention as more particularly defined in the claims that now follow.

What is claimed is:

1. A compound

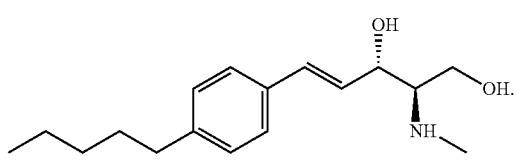 [SMILES: CCCCCc1ccc(/C=C/[C@H](O)[C@@H](CO)NC)cc1]

2. A composition comprising the compound of claim 1, wherein the composition inhibits sphingosine kinase 1 (SphK1) at least five times greater than it inhibits sphingosine kinase 2 (SphK2) in an in vitro assay that measures sphingosine kinase activity.

3. A pharmaceutical composition comprising the compound of claim 1.

4. A compound

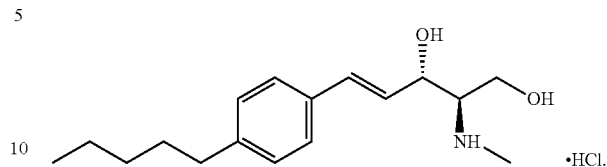

5. A pharmaceutical composition comprising the compound of claim 4.

* * * * *

UNITED STATES PATENT AND TRADEMARK OFFICE
CERTIFICATE OF CORRECTION

PATENT NO. : 8,372,888 B2
APPLICATION NO. : 12/387228
DATED : February 12, 2013
INVENTOR(S) : Robert Elliot Zipkin, Sarah Spiegel and Jeffrey Kroll Adams It is certified that error appears in the above-identified patent and that said Letters Patent is hereby corrected as shown below:

In the Specification

Column 1, line 8, under the title, please insert the following sentence:

-- This invention was made with government support under Grant R01 CA61774 awarded by the National Cancer Institute (NCI). The government has certain rights in the invention. --

Signed and Sealed this
Nineteenth Day of May, 2015

Michelle K. Lee
*Director of the United States Patent and Trademark Office*